US011957776B2

(12) United States Patent
Lee et al.

(10) Patent No.: US 11,957,776 B2
(45) Date of Patent: *Apr. 16, 2024

(54) HAIR COMPOSITIONS

(71) Applicant: L'OREAL, Paris (FR)

(72) Inventors: Heather Lee, Springfield, PA (US); Jung Hyun Park, Westfield, NJ (US); Kristin Jones, Old Bridge, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/730,382

(22) Filed: Apr. 27, 2022

(65) Prior Publication Data

US 2022/0354762 A1 Nov. 10, 2022

Related U.S. Application Data

(60) Provisional application No. 63/181,589, filed on Apr. 29, 2021.

(30) Foreign Application Priority Data

Jul. 9, 2021 (FR) ...................................... 2107454

(51) Int. Cl.
| | | |
|---|---|---|
| *A61K 8/33* | (2006.01) | |
| *A61K 8/34* | (2006.01) | |
| *A61K 8/37* | (2006.01) | |
| *A61K 8/41* | (2006.01) | |
| *A61K 8/42* | (2006.01) | |
| *A61K 8/44* | (2006.01) | |
| *A61Q 5/12* | (2006.01) | |

(52) U.S. Cl.
CPC ................ *A61K 8/375* (2013.01); *A61K 8/33* (2013.01); *A61K 8/34* (2013.01); *A61K 8/342* (2013.01); *A61K 8/345* (2013.01); *A61K 8/37* (2013.01); *A61K 8/416* (2013.01); *A61K 8/42* (2013.01); *A61K 8/44* (2013.01); *A61Q 5/12* (2013.01)

(58) Field of Classification Search
CPC . A61K 8/375; A61K 8/33; A61K 8/34; A61K 8/342; A61K 8/345; A61K 8/37; A61K 8/416; A61K 8/42; A61K 8/44; A61K 8/41; A61Q 5/12
USPC .......................................................... 424/70
See application file for complete search history.

(56) References Cited

U.S. PATENT DOCUMENTS

| | | |
|---|---|---|
| 4,859,456 A | 8/1989 | Marschner |
| 5,888,489 A | 3/1999 | von Mallek |
| 6,342,238 B1 | 1/2002 | Simonnet et al. |
| 6,620,409 B2 | 9/2003 | Bossmann et al. |
| 7,041,142 B2 | 5/2006 | Chan et al. |
| 8,486,425 B1 | 7/2013 | Shah et al. |
| 10,004,673 B1 | 6/2018 | Elsen-Wahrer et al. |
| 2007/0292461 A1 | 12/2007 | Tamarkin et al. |
| 2013/0034515 A1 | 2/2013 | Stone et al. |
| 2016/0235651 A1 | 8/2016 | Decoster et al. |
| 2018/0280270 A1 | 10/2018 | Rughani et al. |
| 2018/0311131 A1 | 11/2018 | Perner et al. |
| 2019/0365628 A1 | 12/2019 | Kolde et al. |

FOREIGN PATENT DOCUMENTS

| | | | |
|---|---|---|---|
| KR | 1020080010846 A | 1/2008 | |
| KR | 20100081509 A | 7/2010 | |
| KR | 1020130046109 A | 5/2013 | |
| KR | 1020130049305 A | 5/2013 | |
| WO | 02102351 A2 | 12/2002 | |
| WO | 03037281 A1 | 5/2003 | |
| WO | 2018178341 A1 | 10/2018 | |
| WO | 2018218000 A1 | 11/2018 | |
| WO | WO-2019207447 A1 * | 10/2019 | ......... A45D 19/0066 |
| WO | WO-2020182318 A1 * | 9/2020 | ............... A61K 8/24 |
| WO | 2021202656 A1 | 10/2021 | |
| WO | 2022046597 A1 | 3/2022 | |

OTHER PUBLICATIONS

Toshiyuki, Iwata et al., "Effect of the Behenyl Trimethyl Ammonium Counterion on the Lamellar Gel Property," International Federation of Societies of Cosmetic Chemists Magazine, No. 4, 2013, pp. 249-255.
International Search Report and Written Opinion dated Aug. 26, 2022 for corresponding PCT Application No. PCT/US2022/026445.

* cited by examiner

Primary Examiner — Frederick F Krass
Assistant Examiner — Lucy M Tien
(74) Attorney, Agent, or Firm — POLSINELLI PC

(57) ABSTRACT

Hair compositions and methods for caring for and providing cosmetic benefits to the hair using the compositions are disclosed. The hair care compositions may include about 50 to about 90 wt. % of a polyol; about 0.1 to about 10 wt. % of fatty compounds, the fatty compounds comprising a carbonate and a fatty ether; about 10 to about 35 wt. % of a monoalcohol; and about 0.1 to about 5 wt. % of a cationic surfactant, wherein all weight percentages are based on the total weight of the hair composition. The hair care composition may be formulated to have a weight ratio of the total amount of carbonate to the total amount of fatty ether is about 3:1 to about 1:1.

19 Claims, 1 Drawing Sheet

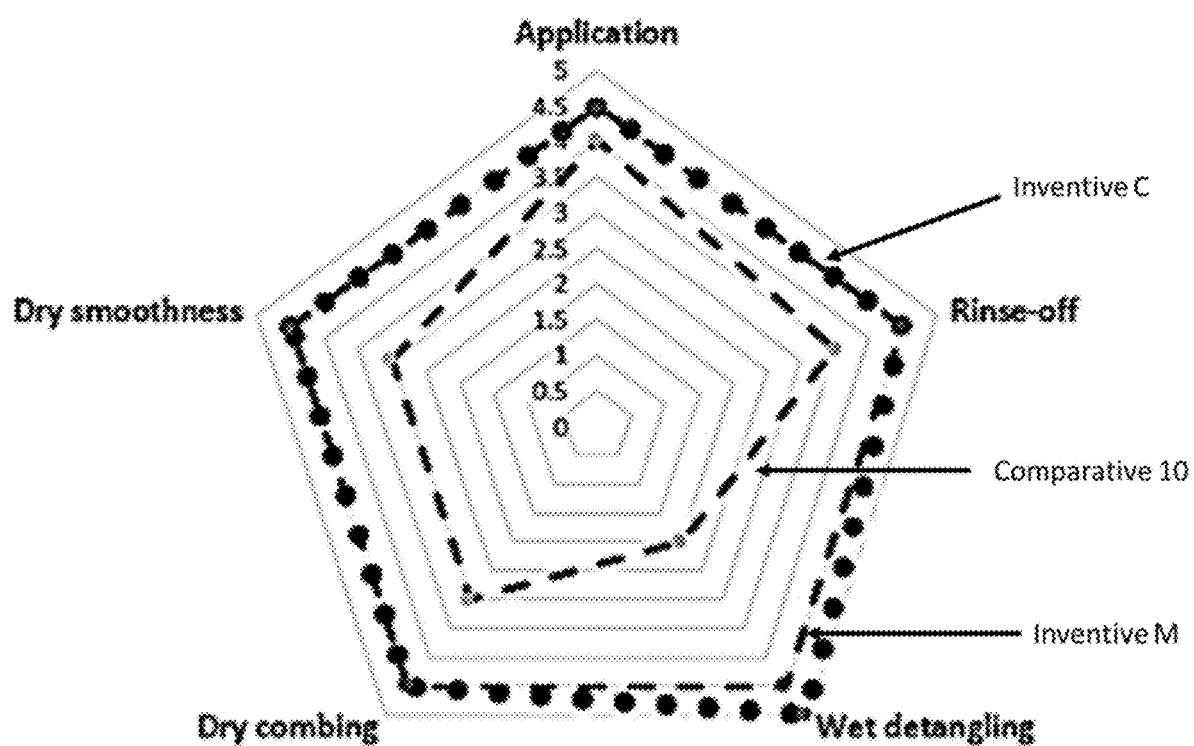

HAIR COMPOSITIONS

CROSS-REFERENCE TO RELATED APPLICATIONS

This application claims benefit of U.S. Ser. No. 63/181,589, filed Apr. 29, 2021, and benefit of French Application No. FR 2107454, filed on Jul. 9, 2021, which are incorporated herein by reference in their entirety.

FIELD OF THE DISCLOSURE

The present disclosure relates to hair care and treatment compositions and to methods for caring for and providing cosmetic benefits to the hair using the compositions.

BACKGROUND OF THE DISCLOSURE

Many individuals suffer from dry and damaged hair. Dryness and damage can occur due to several factors including weather exposure, mechanical treatments (e.g. brushing hair), excessive treatments using chemicals, dying hair, heat styling, etc. In combination, the use of cleansing products that can excessively strip hair's natural oils, can also lead to split ends, dull hair, and exacerbate dry hair. To mitigate the damage, oil treatments, conditioner, hair masks, and chemical treatments are commonly used.

The popularity and usage of oils for dry hair treatments has increased due to their effectiveness and simplicity. Commonly used oils include olive oil, mineral oil, avocado oil, apricot kernel oil, rice bran oil, and coconut oil. However, one problem is that effects are not usually seen after more than several hours (e.g., 8 hours) of treatment and several treatments are usually required, making it time consuming and labor intensive.

Individuals desire a treatment for hair or damaged hair that is not time consuming and labor intensive to use. A variety of approaches have been developed to condition the hair. A common method of providing conditioning benefit is through the use of rinse-off and leave-on hair conditioners and masks containing conditioning agents, such as cationic surfactants and polymers, high melting point fatty compounds, low melting point oils, silicone compounds, and mixtures thereof. Such products typically contain a substantial amount of water or are in the form of emulsions.

However, there could still be some drawbacks to conventional conditioner products, such as being too heavy on the hair or weighing down the hair and/or being greasy. In addition, some products may not sufficiently condition or improve the sensorial feel of the hair or reduce the damaged feel of hair. Thus, there is still a need for providing hair care or hair treatment products which provide improved hair manageability, for example, improved hair alignment and reduced unwanted volume (especially reduced frizz), as well as hair repair benefits or less damaged feel to hair (especially for damaged hair), a weightless feel on hair (hair is not weighed down) and improved overall appearance of the hair. There is also a need to develop hair care products that can impart other benefits at the same time in addition to caring and conditioning benefits, such as improved shine, detangling, ease of combing, smoothness, shape, discipline, and sealed ends of the hair desirable volume, curl definition (for curly or wavy hair), and restylability or reshaping (without the need to reapply the product).

SUMMARY OF THE DISCLOSURE

The present disclosure relates to hair care and treatment compositions and to methods for caring for and providing cosmetic benefits to the hair using the compositions. The inventors discovered that hair compositions formulated with certain combinations of ingredients in specific weight ratios achieved unexpected sensorial benefits to hair. For instance, it was discovered that hair compositions having specific combinations of carbonates and fatty ethers in certain weight ratios synergistically provide enhanced sensorial feel (such as improved smooth, silky, and natural hair feel). Additionally, certain hair compositions having unique combinations of carbonates and fatty ethers in certain weight ratios unexpectedly provided the synergistically enhanced sensorial feel in addition to improved hair repair. The inventors discovered that the hair care compositions having certain chelants, such as tetrasodium glutamate diacetate, unexpected achieved improved solvation and color stability.

The hair compositions according to an aspect of the disclosure typically include:
(a) about 50 to about 90 wt. % of a polyol;
(b) about 0.5 to about 10 wt. % of fatty compounds, the fatty compounds comprising a carbonate and a fatty ether,
wherein a weight ratio of the total amount of carbonate to the total amount of fatty ether is about 3:1 to about 1:1,
(c) about 10 to about 35 wt. % of a monoalcohol; and
(d) about 0.1 to about 5 wt. % of a cationic surfactant,
wherein all weight percentages are based on the total weight of the hair composition.

The hair compositions may be formulated with a weight ratio of the polyol to the monoalcohol(s) (polyol:monoalcohol(s)) that is from 20:1 to 1:1. In at least one instance, the monoalcohol is ethanol.

The polyol may be a glycol chosen from ethylene glycol, propylene glycol, butylene glycol, hexylene glycol, pentylene glycol, diethylene glycol, dipropylene glycol, and a mixture thereof.

The hair compositions may further comprise about 0.1 to about 5 wt. % of an acid chosen from citric acid, tartaric acid, lactic acid, and a mixture thereof. In some cases, the acid is chosen from tartaric acid, lactic acid, a salt thereof, and a mixture thereof.

In some cases, the fatty ether is dicapryl ether and the carbonate is dicaprylyl carbonate. The fatty compounds of the hair composition may further comprise up to 2 wt. % of fatty alcohol chosen from cetearyl alcohol, stearyl alcohol, behenyl alcohol, cetyl alcohol, myristyl alcohol, isostearyl alcohol, lauryl alcohol, oleyl alcohol, and a mixture thereof. In one instance, the fatty compounds further comprises oleyl alcohol.

Additionally or alternatively, the hair composition may be formulated to have a weight ratio of the total amount of fatty alcohol to the total amount of cationic surfactant is about 2:1 to about 1:2. Non-limiting examples of cationic surfactants may be chosen from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, stearamidopropyl dimethylamine, isostearamidopropyl dimethylamine, oleyl hydroxyethyl imidazoline, behenamidopropyldimethylamine, behenamidopropyldiethylamine, behenamidoethyldiethyl-amine, behenamidoethyldimethylamine, arachidamidopropyldimethylamine, arachidamidopropyidiethylamine, arachidamidoethyidiethylamine, arachidamidoethyidimethylamine, and a mixture thereof.

In some cases, the hair composition may further comprise about 0.1 to about 5 wt. % of a chelant. Suitable examples of chelants include tetrasodium glutamate diacetate. The hair composition may have less than 1 wt. % of water.

According to another aspect of the disclosure, a method is provided for treating hair including:
(I) applying a hair composition to wet or dam hair, the hair composition comprising:
  (a) about 50 to about 90 wt. % of a polyol;
  (b) about 0.5 to about 10 wt. % of fatty compounds, the fatty compounds comprising one or more fatty ethers and one or more carbonates,
    wherein a weight ratio of the total amount of carbonate to the total amount of fatty ether is about 3:1 to about 1:1,
  (c) about 10 to about 35 wt. % of a monoalcohol; and
  (d) about 0.1 to about 5 wt. % of a cationic surfactant,
    wherein all weight percentages are based on the total weight of the hair composition.

The method, when treating hair, may include
conditioning the hair;
providing curl definition to the hair;
providing frizz control to the hair;
improving ease of combability and detangling;
protecting the hair from damage;
increasing the appearance of hair volume;
imparting or improving shine on hair; or
a combination thereof.

BRIEF DESCRIPTION OF THE FIGURES

Implementation of the present technology will now be described, by way of example only, with reference to the attached figures, wherein:

FIG. 1 provides a graph summarizing the evaluation of two exemplary compositions and a comparative composition in accordance with aspects of the disclosure.

It should be understood that the various aspects are not limited to the arrangements and instrumentality shown in the drawings.

DETAILED DESCRIPTION OF THE DISCLOSURE

The present disclosure relates to hair care and treatment compositions and to methods for caring for and providing cosmetic benefits to the hair using the compositions.

The inventors discovered that hair compositions formulated with certain combinations of ingredients in specific weight ratios achieved unexpected sensorial benefits to hair. For instance, it was discovered that hair compositions having specific combinations of carbonates and fatty ethers in certain weight ratios synergistically provide enhanced sensorial feel (such as improved smooth, silky, and natural hair feel). Additionally, certain hair compositions having unique combinations of carbonates and fatty ethers in certain weight ratios unexpectedly provided improved hair repair in addition to the synergistically enhanced sensorial feel.

It was further discovered that particular combinations of ingredients have certain spreading values enhanced the sensorial benefits of hair. For example, the hair compositions may include one or more fatty compound having a spreading value of about 500 to 1,000 $mm^2/10$ minutes and one or more fatty compound having a spreading value of greater than 1,000 $mm^2/10$ minutes. In at least one instance, the hair composition includes two or more fatty compounds having a spreading value of about 500 to 1,000 $mm^2/10$ minutes and one or more fatty compound having a spreading value of greater than 1,000 $mm^2/10$ minutes. As referred to herein, the spreading value of an ingredient is determined by measuring the 5 µl of the emollient and/or ingredient applied onto a pretreated collagen foil and image analysis determines the spreading area after 10 minutes. The values are converted to in vivo values based on calibration curves derived from in vivo studies.

The hair composition may be formulated to have a weight ratio of the total amount of fatty compound having a spreading value of about 500 to 1,000 $mm^2/10$ minutes to the total amount of fatty compound having a spreading value of greater than 1,000 $mm^2/10$ minutes that is about 3:1 to about 1:1. In some cases, the weight ratio of the total amount of fatty compound having a spreading value of about 500 to 1,000 $mm^2/10$ minutes to the total amount of fatty compound having a spreading value of greater than 1,000 $mm^2/10$ minutes is about 3:1 to about 1:1, about 2.75:1 to about 1:1, about 2.5:1 to about 1:1, about 2.25:1 to about 1:1, or about 2:1 to about 1:1.

Additionally, the inventors unexpectedly discovered that certain embodiments of the hair compositions comprising one or more acids chosen from citric acid, tartaric acid, lactic acid, and a mixture thereof exhibited enhanced color stability. The inventors were surprised by the enhanced color stability, solvation, and/or solubility of certain hair compositions comprising an acid chosen from tartaric acid, lactic acid, and a mixture thereof. The inventors discovered that the hair care compositions having certain chelants, such as tetrasodium glutamate diacetate, unexpected achieved improved solvation and color stability.

The hair compositions may, surprisingly, achieve many of the foregoing benefits while utilizing ingredients that are or are derived from natural and/or organic sources according to ISO 16128-2:2017. For example, the hair compositions may have about 10 wt. % or more of the ingredients meeting the definition for being natural, organic, natural origin and/or organic origin based on ISO 16128-2:2017. In some cases, the hair compositions have about 20 wt. % or more, about 30 wt. % or more, about 40 wt. % or more, about 50 wt. % or more, about 55 wt. % or more, about 60 wt. % or more, about 65 wt. % or more, about 70 wt. % or more, about 75 wt. % or more, about 80 wt. % or more, or any ranges formed therebetween, of the ingredients meeting the definition for being natural, organic, natural origin and/or organic origin based on ISO 16128-2:2017.

The hair compositions according to an aspect of the disclosure typically include:
(a) about 50 to about 90 wt. % of a polyol;
(b) about 0.5 to about 10 wt. % of fatty compounds, the fatty compounds comprising a carbonate and a fatty ether,
  wherein a weight ratio of the total amount of carbonate to the total amount of fatty ether is about 3:1 to about 1:1,
(c) about 10 to about 35 wt. % of a monoalcohol; and
(d) about 0.1 to about 5 wt. % of a cationic surfactant,
  wherein all weight percentages are based on the total weight of the hair composition.

The hair composition may be formulated to have a weight ratio of the total amount of carbonate to the total amount of fatty ether is about 3:1 to about 1:1. In some cases, the weight ratio of the total amount of carbonate to the total amount of fatty ether is about 3:1 to about 1:1, about 2.75:1 to about 1:1, about 2.5:1 to about 1:1, about 2.25:1 to about 1:1, or about 2:1 to about 1:1.

The present disclosure also relates to methods of treating or caring for the hair comprising applying onto hair the hair compositions of the present disclosure. In various embodiments, the compositions of the present disclosure provide to hair one or more of improved shine, detangling, ease of combing, smoothness, sleekness, shape, discipline, sealed ends of the hair, desirable volume, weightless feel (does not weigh the hair down), and curl care and definition (for curly or wavy hair).

The term "transparent" with respect to a transparent composition indicates that the composition has transmittance of at least 80% at a wavelength of 600 nm, for example measured using a Lambda 40 UV-visible spectrometer. The compositions may have, for example, a transmittance of at least 80%, at least 90%, or at least 95% at a wavelength of 600 nm, measured, for example, using a Lambda 40 UV-visible spectrometer. The term "transparent" is interchangeable with the term "clear" for purposes of the instant disclosure. The term "transparent" can also mean that an article is visible to the human eye when looking through the composition contained in a clear glass bottle.

The hair compositions can be substantially anhydrous. The phrase "substantially anhydrous" is interchangeable with the phrase "essentially free of water" or "substantially free of water." A substantially anhydrous composition may include up to 10 wt. % of water regardless of whether the water is added to the composition or part of a raw material. Nonetheless, the substantially anhydrous composition may include less than 9 wt. %, less than 8 wt. %, less than 7 wt. %, less than 6 wt. %, less than 5 wt. %, less than 4 wt. %, less than 3 wt. %, less than 2 wt. %, less than 1 wt. %, or less than 0.5 wt. % of water. The hair compositions can be anhydrous, that is, they do not contain water or are free of water (added water or part of a raw material).

The hair compositions of the instant disclosure typically have a viscosity at 25° C. of about 10 mPa·s to about 10,000 mPa·s or about 10 mPa·s to about 8,000 mPa·s, or about 10 mPa·s to about 6,000 mPa·s, or about 10 mPa·s to about 4,000 mPa·s, or about 10 mPa·s to about 2,000 mPa·s, or about 10 mPa·s to about 1,000 mPa·s, or about 10 mPa·s to about 800 mPa·s, or about 10 mPa·s to about 600 mPa·s, or about 10 mPa·s to about 500 mPa·s, or about 10 mPa·s to <500 mPa·s, including ranges and sub-ranges there between. The viscosity measurements can be carried out, for example, using a Brooksfield viscometer, Model RVT (Brookfield Engineering Laboratories, Inc.) at about 20 revolutions per minute (RPM), at ambient room temperature of about 20 to 25° C.; spindle sizes may be selected in accordance with the standard operating recommendations form the manufacturer, ranging from disk spindle No. 1 to No. 4.

The pH of the hair composition typically is 2.5 to 5.5. For example, the pH of the hair composition may be from 2.5 to about 5.25, 2.5 to about 5, 2.5 to about 4.75, 2.5 to about 4.5, 2.5 to about 4.25, 2.5 to about 4, 2.5 to about 3.75, 2.5 to about 3.5, 2.5 to about 3.25, 2.5 to about 3; about 2.75 to 5.5, about 2.75 to about 5.25, about 2.75 to about 5, about 2.75 to about 4.75, about 2.75 to about 4.5, about 2.75 to about 4.25, about 2.75 to about 4, about 2.75 to about 3.75, about 2.75 to about 3.5; about 3 to 5.5, about 3 to about 5.25, about 3 to about 5, about 3 to about 4.75, about 3 to about 4.5, about 3 to about 4.25, about 3 to about 4, about 3 to about 3.75; about 3.25 to 5.5, about 3.25 to about 5.25, about 3.25 to about 5, about 3.25 to about 4.75, about 3.25 to about 4.5, about 3.25 to about 4.25, about 3.25 to about 4; about 3.5 to 5.5, about 3.5 to about 5.25, about 3.5 to about 5, about 3.5 to about 4.75, about 3.5 to about 4.5, about 3.5 to about 4.25; about 3.75 to 5.5, about 3.75 to about 5.25, about 3.75 to about 5, about 3.75 to about 4.75, about 3.75 to about 4.5; about 4 to 5.5, about 4 to about 5.25, about 4 to about 5, about 4 to about 4.75; about 4.25 to 5.5, about 4.25 to about 5.25, about 4.25 to about 5; about 4.25 to about 5.25, about 4.25 to about 5, about 4 to about 4.75; about 4.25 to about 5.25, or about 4.25 to about 5, ranges and subranges therebetween.

Suitable components, such as those listed below, may be included or excluded from the formulations for the skin-tightening compositions depending on the specific combination of other components, the form of the skin-tightening compositions, and/or the use of the formulation.

Polyol(s)

The hair compositions include one or more polyols, e.g., such as those chosen from ethylene glycol, propylene glycol, butylene glycol, hexylene glycol, pentylene glycol, diethylene glycol, dipropylene glycol, 1,3 propanediol, glycerin, diglycerin, and a mixture thereof. The amount of polyol(s) present in the hair composition typically ranges from about 50 wt. % or higher, based on the total weight of the hair composition. For example, the amount of polyol(s) in the hair composition may be about 50 to about 90 wt. %, about 50 to about 87 wt. %, about 50 to about 85 wt. %, about 50 to about 80 wt. %, about 50 to about 75 wt. %, about 50 to about 70 wt. %, about 50 to about 65 wt. %, about 50 to about 60 wt. %; about 60 to about 90 wt. %, about 60 to about 87 wt. %, about 60 to about 85 wt. %, about 60 to about 80 wt. %, about 60 to about 75 wt. %, about 60 to about 70 wt. %; about 65 to about 90 wt. %, about 65 to about 87 wt. %, about 65 to about 85 wt. %, about 65 to about 80 wt. %, about 65 to about 75 wt. %; about 70 to about 90 wt. %, about 70 to about 87 wt. %, about 70 to about 85 wt. %, about 70 to about 75 wt. %, including all ranges and sub-ranges therebetween, based on the total weight of the hair composition.

The term "polyol" should be understood as meaning, within the meaning of the present disclosure, an organic molecule comprising at least two free hydroxyl groups. The polyols of the hair composition may be glycols or compounds with numerous hydroxyl groups. In some cases, the one or more polyols is/are selected from the group consisting of $C_2$-$C_{32}$ polyols. The one or more polyols may be liquid at ambient temperature (25° C.). The one or more polyols may have from 2 to 32 carbon atoms, from 3 to 16 carbon atoms, or from 3 to 12 carbon atoms.

Polyols that may be included in the hair composition, in certain instances, include ethylene glycol, propylene glycol, butylene glycol, hexylene glycol, pentylene glycol, 1,3-propanediol, dipropylene glycol, caprylyl glycol, glycerin, diglycerin, diethylene glycol, and dipropylene glycol, and mixtures thereof. In some cases, the polyol is propylene glycol. In some further cases, the polyol is one or both of propylene glycol and butylene glycol. Additionally, in some cases, the hair composition comprises at least propylene glycol, and optionally one or more polyols other than propylene glycol.

Non-limiting examples of polyols that may be included in the hair composition include and/or may be chosen from alkanediols such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, dipropylene glycol mono-iso-propyl ether, sorbitol, sorbitan, triacetin, and a mixture thereof.

The one or more polyols may, optionally, be glycols or glycol ethers such as, e.g., monomethyl, monoethyl and monobutyl ethers of ethylene glycol, propylene glycol or ethers thereof such as, e.g., monomethyl ether of propylene glycol, butylene glycol, hexylene glycol, dipropylene glycol as well as alkyl ethers of diethylene glycol, e.g., monoethyl ether or monobutyl ether of diethylene glycol.

Fatty Compound(s)

The hair composition includes a fatty compound(s). The amount of fatty compound(s) may be from about 0.1 to about 10 wt. % of the total weight of the hair composition. In some instances, the fatty compounds(s) are in an amount ranging from about 0.1 to about 10 wt. %, about 0.1 to about 9 wt. %, about 0.1 to about 8 wt. %, about 0.1 to about 7 wt. %, about 0.1 to about 6 wt. %, about 0.1 to about 5 wt. %, about 0.1 to about 4 wt. %, about 0.1 to about 3 wt. %; about 0.2 to about 10 wt. %, about 0.2 to about 9 wt. %, about 0.2 to about 8 wt. %, about 0.2 to about 7 wt. %, about 0.2 to about 6 wt. %, about 0.2 to about 5 wt. %, about 0.2 to about 4 wt. %, about 0.2 to about 3 wt. %; about 0.5 to about 10 wt. %, about 0.5 to about 9 wt. %, about 0.5 to about 8 wt. %, about 0.5 to about 7 wt. %, about 0.5 to about 6 wt. %, about 0.5 to about 5 wt. %, about 0.5 to about 4 wt. %, about 0.5 to about 3 wt. %; about 1 to about 10 wt. %, about 1 to about 9 wt. %, about 1 to about 8 wt. %, about 1 to about 7 wt. %, about 1 to about 6 wt. %, about 1 to about 5 wt. %, about 1 to about 4 wt. %, about 1 to about 3 wt. %; about 1.5 to about 10 wt. %, about 1.5 to about 9 wt. %, about 1.5 to about 8 wt. %, about 1.5 to about 7 wt. %, about 1.5 to about 6 wt. %, about 1.5 to about 5 wt. %, about 1.5 to about 4 wt. %, about 1.5 to about 3 wt. %; about 2 to about 10 wt. %, about 2 to about 9 wt. %, about 2 to about 8 wt. %, about 2 to about 7 wt. %, about 2 to about 6 wt. %, about 2 to about 5 wt. %, about 2 to about 4 wt. %, about 2 to about 3 wt. %; about 3 to about 10 wt. %, about 3 to about 9 wt. %, about 3 to about 8 wt. %, about 3 to about 7 wt. %, about 3 to about 6 wt. %, about 3 to about 5 wt. %; about 4 to about 10 wt. %, about 4 to about 9 wt. %, about 4 to about 8 wt. %, about 4 to about 7 wt. %, about 4 to about 6 wt. %, about 4 to about 5 wt. %, including ranges and sub-ranges therebetween, based on the total weight of the hair composition.

Examples of fatty compound(s) that may be incorporated into the hair composition include fatty alcohol, a fatty ester, a fatty ether, a fatty acid, a wax, an oil, a derivative thereof, and a mixture thereof. Additional examples of fatty compounds that are worth mentioning include oils, mineral oil, alkanes (paraffins), fatty alcohol derivatives, fatty acid derivatives, esters of fatty alcohols, hydroxy-substituted fatty acids, waxes, triglyceride compounds, lanolin, and a mixture thereof. One or more fatty compounds(s) may be included in the hair composition has an emulsifier. For example, the fatty compound may be a fatty alcohol that is capable of or is used for emulsifying another ingredient. Although not specifically identified, some of the fatty compounds listed below may be utilized as emulsifiers. Further examples of fatty compounds are discussed below.

Fatty Ester(s)

The hair compositions may include one or more fatty compound(s) that is a fatty ester. For example, the fatty compound(s) may be chosen from dialkyl carbonates of formula: $R_1O(C=O)R_2$, wherein $R_1$ and $R_2$ are independently linear or branched, saturated or unsaturated alkyl chains having 1 to 30 carbon atoms, or having 2 to 28 carbon atoms, or having 4 to 25 carbon atoms, or having 6 to 22 carbon atoms, preferably one or more fatty carbonates selected from C14-15 dialkyl carbonate, dicaprylyl carbonate, diethyl carbonate, dihexyl carbonate, diethylhexyl carbonate, dimethoxyphenyl phenyloxoethyl ethylcarbonate, dimethyl carbonate, dipropyl carbonate, dipropylheptyl carbonate, dioctyl carbonate, and a mixture thereof.

Additionally or alternatively, the fatty ester chosen from cetyl ester, purcellin oil (cetearyl octanoate), isopropyl myristate, isopropyl palmitate, $C_{12}$-$C_{15}$ alkyl benzoate, 2-ethylphenyl benzoate, isopropyl lanolate, hexyl laurate, diisopropyl adipate, isononyl isononanoate, oleyl erucate, 2-ethylhexyl palmitate, isostearyl isostearate, diisopropyl sebacate, octanoates, decanoates or ricinoleates of alcohols or polyalcohols, hydroxylated esters, dicaprylyl carbonate, pentaerythritol esters, and a mixture thereof. Other fatty esters worth mentioning include polyglyceryl-10 oleate, polyglyceryl-10 dioleate, polyglyceryl-6 stearate, polyglyceryl-6 distearate, polyglyceryl-10 stearate, polyglyceryl-10 distearate, polyglyceryl-8 dipalmitate, polyglyceryl-10 dipalmitate, polyglyceryl-10 behenate, and polyglyceryl-12 trilaurate.

Fatty Carbonate Ester(s)

The fatty compounds comprise one or more carbonate esters (also referred to as "fatty carbonates"). Fatty carbonate esters include dialkyl carbonates. Non-limiting examples of dialkyl carbonates include those of the following formula: $R_1O(C=O)OR_2$, wherein $R_1$ and $R_2$ are independently linear or branched, saturated or unsaturated alkyl chains having 1 to 30 carbon atoms, or having 2 to 28 carbon atoms, or having 4 to 25 carbon atoms, or having 6 to 22 carbon atoms, for example, C14-15 dialkyl carbonate, dicaprylyl carbonate, diethyl carbonate, dihexyl carbonate, diethylhexyl carbonate, dimethoxyphenyl phenyloxoethyl ethylcarbonate, dimethyl carbonate, dipropyl carbonate, dipropylheptyl carbonate, dioctyl carbonate, and a mixture thereof. In some instances, it is preferable to include one or more dialkyl carbonates, in particular dicaprylyl carbonate.

The total amount of the one or more fatty carbonate ester(s) in the composition can vary but is typically about 3 wt. % or less, 2 wt. % or less, or 1 wt. % or less, based on the total weight of the composition. In some cases, the total amount of fatty carbonate ester(s) is from about 0.05 to about 3 wt. %, about 0.05 to about 2.5 wt. %, about 0.05 to about 2 wt. %, about 0.05 to about 1.5 wt. %, about 0.05 to about 1 wt. %; about 0.1 to about 3 wt. %, about 0.1 to about 2.5 wt. %, about 0.1 to about 2 wt. %, about 0.1 to about 1.5 wt. %, about 0.1 to about 1 wt. %; about 0.25 to about 3 wt. %, about 0.25 to about 2.5 wt. %, about 0.25 to about 2 wt. %, about 0.25 to about 1.5 wt. %, about 0.25 to about 1 wt. %; about 0.5 to about 3 wt. %, about 0.5 to about 2.5 wt. %, about 0.5 to about 2 wt. %, about 0.5 to about 1.5 wt. %, about 0.5 to about 1 wt. %; about 0.75 to about 3 wt. %, about 0.75 to about 2.5 wt. %, about 0.75 to about 2 wt. %, about 0.75 to about 1.5 wt. %, about 0.75 to about 1 wt. %, including ranges and sub-ranges there between, based on the total weight of the composition. In other cases, the total amount of fatty carbonate ester(s) is from about 0.05 to about 1 wt. %, about 0.07 to about 1 wt. %, about 0.08 to about 1 wt. %, about 0.1 to about 0.9 wt. %, about 0.2 to about 0.7 wt. %, about 0.3 to about 0.6 wt. %, or about 0.3 to about 0.5 wt. %, including ranges and sub-ranges there between, based on the total weight of the composition.

Fatty Ether(s)

The fatty compounds comprise one or more fatty ethers. For example, the hair composition may include olyoxyethylene cetyl/stearyl ether, polyoxyethylene cholesterol ether, polyoxyethylene laurate or dilaurate, polyoxyethylene stearate or distearate, polyoxyethylene lauryl or stearyl ether, dicaprylyl ether, dicetyl ether distearyl ether, or a mixture thereof. Non-limiting examples of suitable polyoxyethylene fatty ethers include, but are not limited to, polyoxyethylene cetyl/stearyl ether, polyoxyethylene cholesterol ether, polyoxyethylene laurate or dilaurate, polyoxyethylene stearate or distearate, polyoxyethylene lauryl or stearyl ether, and mixtures thereof, wherein the polyoxyethylene head group ranges from about 2 to about 100 groups. In certain embodiments, the polyoxyethylene fatty ethers include polyoxyethylene stearyl ether, polyoxyethylene myristyl ether, polyoxyethylene lauryl ether having from about 3 to about 10 oxyethylene units and mixtures thereof.

The fatty ether may be a dialkyl ether. Non-limiting examples of dialkyl ethers include dicaprylyl ether, dicetyl ether, dodecyl ether, dilauryl ether, dimyristyl ether, distearyl ether, diisononyl ether, and a mixture thereof.

The total amount of the one or more fatty ether(s) in the composition can vary but is typically about 3 wt. % or less, about 2 wt. % or less, or about 1 wt. % or less, based on the total weight of the hair composition.

In some cases, the total amount of dialkyl ether(s) is about 0.05 to about 3 wt. %, about 0.05 to about 2.5 wt. %, about 0.05 to about 2 wt. %, about 0.05 to about 1.5 wt. %, about 0.05 to about 1 wt. %; about 0.1 to about 3 wt. %, about 0.1 to about 2.5 wt. %, about 0.1 to about 2 wt. %, about 0.1 to about 1.5 wt. %, about 0.1 to about 1 wt. %; about 0.25 to about 3 wt. %, about 0.25 to about 2.5 wt. %, about 0.25 to about 2 wt. %, about 0.25 to about 1.5 wt. %, about 0.25 to about 1 wt. %; about 0.5 to about 3 wt. %, about 0.5 to about 2.5 wt. %, about 0.5 to about 2 wt. %, about 0.5 to about 1.5 wt. %, about 0.5 to about 1 wt. %; about 0.75 to about 3 wt. %, about 0.75 to about 2.5 wt. %, about 0.75 to about 2 wt. %, about 0.75 to about 1.5 wt. %, about 0.75 to about 1 wt. %, including ranges and sub-ranges there between, based on the total weight of the hair composition.

In other instances, the amount of fatty ether in the hair composition is from about 0.05 to about 1 wt. %, about 0.07 to about 1 wt. %, about 0.08 to about 1 wt. %, about 0.1 to about 0.9 wt. %, about 0.2 to about 0.7 wt. %, about 0.3 to about 0.6 wt. %, or about 0.3 to about 0.5 wt. %, including ranges and sub-ranges there between, based on the total weight of the composition. In certain embodiments, the total amount of the one or fatty ether(s) in the composition is about 1 wt. %, 0.9 wt. %, 0.8 wt. %, 0.7 wt. %, 0.6 wt. %, 0.5 wt. %, 0.4 wt. %, 0.3 wt. %, 0.2 wt. %, 0.1 wt. %, 0.08 wt. %, 0.07 wt. %, 0.06 wt. %, 0.05 wt. %, 0.04 wt. %, 0.03 wt. %, 0.02 wt. %, or 0.01 wt. %, based on the total weight of the composition.

The total amount of fatty carbonate ester(s) is typically at least the same or higher than the total amount of the dialkyl ether(s) in the compositions. The compositions may include more fatty carbonate ester(s) than dialkyl ether(s), i.e., a higher weight percent of the composition is a fatty carbonate ester(s) than dialkyl ether(s). The ratio of fatty carbonate ester(s) to the total amount of dialkyl ether(s) (fatty carbonate ester(s): dialkyl ether(s)) may be from about 2:1 to 1:1, about 2:1 to 1.1:1, about 2:1 to 1.2:1, about 2;1 to 1.3:1, about 2:1 to 1.4:1, about 2:1 to 1.5:1, about 2:1 to 1.6:1, about 2:1 to 1:7:1, or about 2:1 to 1.8:1, including ranges and sub-ranges there between.

Fatty Alcohol(s)

Suitable fatty alcohols, if present, include those having a fatty group with a carbon chain of greater than 8 carbon atoms, 8 to 50 carbon atoms, 8 to 40 carbon atoms, 8 to 30 carbon atoms, 8 to 22 carbon atoms, 12 to 22 carbon atoms, or 12 to 18 carbon atoms, including all ranges and subranges therebetween. In some instances, the fatty group of the fatty alcohols has a carbon chain of 10 to 20 carbon atoms or 10 to 18 carbon atoms. The fatty alcohols may be chosen from polyethylene glycol ethers, such as those having a fatty alcohol group with a carbon chain of 12 to 16 or 12 to 14 carbon atoms.

The fatty alcohol portion is preferably hydrogenated (for example, stearyl, lauryl, cetyl, cetearyl); however, the fatty alcohol may contain one or more double bonds (for example, oleyl). Non-limiting examples of fatty alcohols include decyl alcohol, undecyl alcohol, dodecyl alcohol, myristyl alcohol, lauryl alcohol, cetyl alcohol, stearyl alcohol, cetearyl alcohol (cetyl alcohol and stearyl alcohol), isostearyl alcohol, isocetyl alcohol, behenyl alcohol, linalool, oleyl alcohol, cis-4-t-butylcyclohexanol, isotridecyl alcohol, myricyl alcohol, and a mixture thereof. In some cases, the fatty alcohols comprise at least one of or may be chosen from myristyl alcohol, lauryl alcohol, cetyl alcohol, stearyl alcohol, cetearyl alcohol, isostearyl alcohol, oleyl alcohol, isotridecyl alcohol, and a mixture thereof.

The fatty alcohol may be saturated or unsaturated. Exemplary saturated liquid fatty alcohols may be branched and optionally contain in their structure at least one aromatic or non-aromatic ring. In some instances, however, the fatty alcohols are acyclic. Non-limiting examples of liquid saturated fatty alcohols include octyldodecanol, isostearyl alcohol, and 2-hexyldecanol.

Exemplary unsaturated liquid fatty alcohol may include in their structure at least one double or triple bond. For example, the fatty alcohols may include several double bonds (such as 2 or 3 double bond), which may be conjugated or non-conjugated. The unsaturated fatty alcohols can be linear or branched and may be acyclic or include in their structure at least one aromatic or non-aromatic ring. Liquid unsaturated fatty alcohols may include or be chosen from oleyl alcohol, linoleyl alcohol, linolenyl alcohol and undecylenyl alcohol.

The fatty alcohols may be alkoxylated fatty alcohols, e.g., having about 1 to about 100 moles of an alkylene oxide per mole of alkoxylated fatty alcohol. For example, the alkoxylated fatty alcohols may be alkoxylated with about 1 to about 80 moles, about 2 to about 50, about 5 to about 45 moles, about 10 to about 40 moles, or 15 to about 35 mores, including all ranges and subranges therebetween, of an alkylene oxide per mole of alkoxylated fatty alcohol.

As examples of alkoxylated fatty alcohols, steareth (for example, steareth-2, steareth-20, and steareth-21), laureth (for example, laureth-4, and laureth-12), ceteth (for example, ceteth-10 and ceteth-20) and ceteareth (for example, ceteareth-2, ceteareth-10, and ceteareth-20) are mentioned. In at least one instance, the one or more alkoxylated fatty alcohols include steareth-20. In some instances, the one or more alkoxylated fatty alcohols may be exclusively steareth-20.

Additional fatty alcohol derivatives that may, optionally be suitable include methyl stearyl ether; 2-ethylhexyl dodecyl ether; stearyl acetate; cetyl propionate; the ceteth series of compounds, such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyl-dodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Fatty Acid(s)

In some instances, the fatty compounds may be chosen from fatty acids, fatty acid derivatives, esters of fatty acids, hydroxyl-substituted fatty acids, and alkoxylated fatty acids. The fatty acids may be straight or branched chain acids and/or may be saturated or unsaturated. Non-limiting examples of fatty acids include diacids, triacids, and other multiple acids as well as salts of these fatty acids. For example, the fatty acid may optionally include or be chosen from lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Non-limiting examples of polyglycerol esters of fatty acids include those of the following formula:

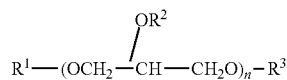

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Non-limiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

Wax(es)

The fatty compounds may, in some instances, include or be chosen from one or more waxes. Non-limiting examples of waxes in this category include for example, synthetic wax, ceresin, paraffin, ozokerite, polyethylene waxes, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, acacia decurrents flower wax, vegetable waxes (such as sunflower seed (*Helianthus annuus*), carnauba, candelilla, ouricury or japan wax or cork fibre or sugarcane waxes), or a mixture thereof.

Oil(s)

The hair compositions include one or more oils. The oil component of the NLCs is typically has melting temperature of less than 45° C., a molecular weight of at least 190, and a solubility in water of no greater than 1 part in 99 parts of water.

Non-limiting examples of include, but are not limited to, natural oils, such as coconut oil; hydrocarbons, such as mineral oil and hydrogenated polyisobutene; esters, such as C12-C15 alkyl benzoate; diesters, such as propylene dipelarganate; and triesters, such as glyceryl trioctanoate. Further examples of oils that may, optionally, be included in the hair compositions include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

Additionally or alternatively, the oil may be selected from plant based and/or vegetable oils. Non-limiting examples of plant-based or vegetable oils include acai oil, almond oil, aloe vera oil, andiroba oil, annatto oil, avocado oil, babassu oil, borage oil, brazil nut oil, buriti oil, camelina oil, coffee oil, copaiba oil, emu oil, passion fruit oil, almond oil, *Ricinus communis* (castor) seed oil, coconut oil, grapeseed oil, jojoba oil, macadamia nut oil, rose hip oil, ajwain oil, angelic root oil, anise oil, aragan oil, asafetida, balsam oil, basil oil, bay oil, bergamot oil, black pepper essential oil, buchu oil, birch oil, camphor, cannabis oil, caraway oil, cardamom seed oil, carrot seed oil, chamomile oil, calamus root oil, cinnamon oil, citronella oil, clary sage, clove leaf oil, coffee, coriander, costmary oil, cranberry seed oil, cubeb, cumin oil, cypress, cypriol, curry leaf, davana oil, dill oil, elecampane, eucalyptus oil, fennel seed oil, fenugreek oil, fir, frankincense oil, galangal, geranium oil, ginger oil, goldenrod, grapefruit oil, grapeseed oil, henna oil, helichrysum, horseradish oil, hyssop, Idaho tansy, jasmine oil, juniper berry oil, lavender oil, lemon oil, lemongrass, marjoram, melaleuca, lemon balm oil, mountain savory, mugwort oil, mustard oil, myrrh oil, myrtle, neem tree oil, neroli, nutmeg, orange oil, oregano oil, orris oil, palo santo, parsley oil, patchouli oil, perilla oil, pennyroyal oil, peppermint oil, petitgrain, pine oil, plum oil, ravensara, red cedar, roman chamomile, rose oil, rosehip oil, rosemary oil, rosewood oil, sandalwood oil, sassafras oil, savory oil, schisandra oil, spikenard, spruce, star anise oil, tangerine, tarragon oil, tea tree oil, thyme oil, tsuga oil, turmeric, valerian, vetiver oil, western red cedar, wintergreen, yarrow oil, ylang-ylang, and zedoary oil.

Non-limiting examples of liquid triglycerides and oils of plant origin include alexandria laurel tree oil, avocado oil, apricot stone oil, barley oil, borage seed oil, calendula oil, canelle nut tree oil, canola oil, caprylic/capric triglyceride castor oil, coconut oil, corn oil, cotton oil, cottonseed oil, evening primrose oil, flaxseed oil, groundnut oil, hazelnut oil, glycereth triacetate, glycerol triheptanoate, glyceryl trioctanoate, glyceryl triundecanoate, hempseed oil, jojoba oil, lucerne oil, maize germ oil, marrow oil, millet oil, neopentylglycol dicaprylate/dicaprate, olive oil, palm oil, passionflower oil, pentaerythrityl tetrastearate, poppy oil, propylene glycol ricinoleate, rapeseed oil, rye oil, safflower oil, sesame oil, shea butter, soya oil, soybean oil, sweet almond oil, sunflower oil, sysymbrium oil, syzigium aromaticum oil, tea tree oil, walnut oil, wheat germ glycerides and wheat germ oil.

Monoalcohol(s)

The hair compositions include monoalcohol(s), such as those having from 2 to 6 carbon atom. The amount of monoalcohol present in the hair composition may range from about 10 to about 35 wt. %, based on the total weight of the hair composition. For example, the hair composition may have monoalcohol in an amount of about 10 to about 35 wt. %, about 10 to about 33 wt. %, about 10 to about 32.5 wt. %, about 10 to about 20 wt. %, about 10 to about 28 wt. %, about 10 to about 26 wt. %; about 12 to about 35 wt. %, about 12 to about 33 wt. %, about 12 to about 32.5 wt. %, about 12 to about 20 wt. %, about 12 to about 28 wt. %, about 12 to about 26 wt. %; about 14 to about 35 wt. %, about 14 to about 33 wt. %, about 14 to about 32.5 wt. %, about 14 to about 20 wt. %, about 14 to about 28 wt. %, about 14 to about 26 wt. %; about 16 to about 35 wt. %, about 16 to about 33 wt. %, about 16 to about 32.5 wt. %, about 16 to about 20 wt. %, about 16 to about 28 wt. %, about 16 to about 26 wt. %; about 18 to about 35 wt. %, about 18 to about 33 wt. %, about 18 to about 32.5 wt. %, about 18 to about 20 wt. %, about 18 to about 28 wt. %, about 18 to about 26 wt. %, including ranges and subranges therebetween, based on the total weight of the hair composition.

The one or more monoalcohols of the hair composition may be chosen from ethanol, propanol, butanol, pentanol, hexanol, isopropyl alcohol, cyclohexanol, isobutyl alcohol, 2-methyl-2-butanol (2-methylbutan-2-ol), and a mixture thereof. In one instance, the one or more monoalcohol(s) includes or consists of ethanol.

The total amount of polyol(s) is typically at least the same or higher than the total amount of the monoalcohol(s) having from 2 to 6 carbon atoms in the compositions. Often, the compositions include more polyol(s) than monoalcohol(s) having from 2 to 6 carbon atoms, i.e., a higher weight percent of the composition is a polyol(s) than monoalcohols having from 2 to 6 carbon atoms. The ratio of polyol(s) to the total amount of monoalcohol(s) having from 2 to 6 carbon atoms (polyol(s): monoalcohol(s)) may be from 20:1 to 1:1. In some instances, the weight ratio of the total amount of polyols to monoalcohols is from about 20:1 to about 1.1:1, about 20:1 to about 1.5:1, about 20:1 to about 2:1; about 18:1 to about 1:1, about 18:1 to about 1.1, about 18:1 to about 1.5:1, about 18:1 to about 2:1, about 15:1 to about 2:1, about 12:1 to about 2:1, about 10:1 to about 2.5:1, about 8:1 to about 2.5:1, about 5:1 to about 2.5:1, or about 5:1 to about 3:1, including ranges and sub-ranges there between.

Additionally or alternatively, the hair composition is formulated to have a weight ratio of propylene glycol to ethanol (propylene glycol:ethanol) that is about 20:1 to about 1.1:1, about 20:1 to about 1.5:1, about 20:1 to about 2:1; about 18:1 to about 1:1, about 18:1 to about 1.1, about 18:1 to about 1.5:1, about 18:1 to about 2:1, about 15:1 to about 2:1, about 12:1 to about 2:1, about 10:1 to about 2.5:1, about 8:1 to about 2.5:1, about 5:1 to about 2.5:1, or about 5:1 to about 3:1, including ranges and sub-ranges there between.

In an embodiment, the hair compositions have a weight ratio of the total amount of polyols to the total amount of monoalcohols (polyol: monoalcohols) is from about 20:1 to about 1:1, 15:1 to about 1:1 or from about 10:1 to about 1.5:1 or from about 8:1 to about 2:1 or from about 5:1 to about 2:1, including ranges and sub-ranges there between. In an embodiment, the one or more polyol(s) is selected from propylene glycol and the one or more monoalcohols is selected from ethanol wherein the weight ratio of propylene glycol to ethanol (propylene glycol:ethanol) is from about 20:1 to about 1:1, about 15:1 to about 1:1 or from about 10:1 to about 1.5:1 or from about 8:1 to about 2:1 or from about 5:1 to about 2:1, including ranges and sub-ranges there between.

Cationic Surfactant(s)

The hair composition includes a cationic surfactant(s). The amount of cationic surfactant(s) may be from about 0.1 to about 5 wt. % of the total weight of the hair composition. In some instances, the cationic surfactant(s) are in an amount ranging from about 0.1 to about 5 wt. %, about 0.1 to about 4 wt. %, about 0.1 to about 3 wt. %; about 0.2 to about 5 wt. %, about 0.2 to about 4 wt. %, about 0.2 to about 3 wt. %; about 0.5 to about 5 wt. %, about 0.5 to about 4 wt. %, about 0.5 to about 3 wt. %; about 1 to about 5 wt. %, about 1 to about 4 wt. %, about 1 to about 3 wt. %; about 1.5 to about 5 wt. %, about 1.5 to about 4 wt. %, about 1.5 to about 3 wt. %; about 2 to about 5 wt. %, about 2 to about 4 wt. %, about 2 to about 3 wt. %; about 3 to about 5 wt. %, about 3 to about 5 wt. %; or about 4 to about 5 wt. %, including ranges and sub-ranges therebetween, based on the total weight of the hair composition.

In an embodiment, the weight ratio of the total amount of fatty alcohols to the total amount of cationic surfactants (fatty alcohols: cationic surfactants) is from about 2:1 to about 1:1, about 2:1 to about 1.1:1, about 2:1 to about 1.2:1, about 2:1 to about 1.3:1, about 2:1 to about 1.4:1, about 2:1 to about 1.5:1, about 2:1 to about 1.6:1, or about 2:1 to about 1.7:1.

The hair composition may include a cationic surfactant that has a carbon chain that is within 10 carbon atoms of the length of the carbon chain of the fatty acid. Suitable cationic surfactants include cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, or mixtures thereof.

Additional, non-limiting examples of cationic surfactants include behenalkonium chloride, benzethonium chloride, cetylpyridinium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectorite, stearyl trihydroxyethyl propylenediamine dihydrofluoride, tallowtrimonium chloride, hexadecyltrimethyl ammonium bromide, and mixtures thereof.

The cationic surfactant(s) may also be chosen from optionally polyoxyalkylenated, primary, secondary or tertiary fatty amines, or salts thereof, and quaternary ammonium salts, and mixtures thereof. In some cases, it is useful to use salts such as chloride salts of the quaternary ammonium compounds.

The fatty amines generally comprise at least one $C_8$-$C_{30}$ hydrocarbon-based chain. For example, quaternary ammonium salts, which may be incorporated in certain instances, include those corresponding to the following general formula:

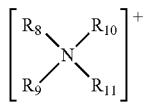

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms and preferably from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyl, alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts having a structure in accordance with the above general formula (III), those that are preferred are, on the one hand, tetraalkylammonium salts, for instance dialkyldimethylammonium or alkyltrimethylammonium salts in which the alkyl group contains approximately from 12 to 22 carbon atoms, such as behenyltrimethylammonium, distearyldimethylammonium, cetyltrimethylammonium or benzyldimethylstearylammonium salts, or, on the other hand, oleocetyldimethylhydroxyethylammonium salts, palmitylamidopropyltrimethylammonium salts, stearamidopropyltrimethylammonium salts and stearamidopropyldimethylcetearylammonium salts.

Examples of quaternary ammonium salt of imidazoline, which may be incorporated in certain instances, include those having a structure according to the general formula provided below:

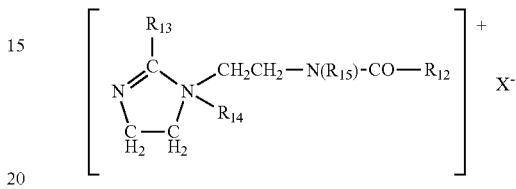

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, alkyl sulfates, alkyl- or alkylarylsulfonates in which the alkyl and aryl groups preferably comprise, respectively, from 1 to 20 carbon atoms and from 6 to 30 carbon atoms. $R_{12}$ and $R_{13}$ preferably denote a mixture of alkenyl or alkyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name REWOQUAT W 75 by the company Rewo.

Examples of quaternary diammonium or triammonium salt, which may be incorporated in certain instances, include those having a structure in accordance with the following general formula:

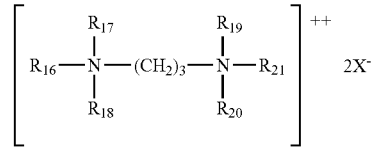

in which $R_{16}$ denotes an alkyl radical comprising approximately from 16 to 30 carbon atoms, which is optionally hydroxylated and/or interrupted with one or more oxygen atoms; $R_{17}$ is chosen from hydrogen or an alkyl radical comprising from 1 to 4 carbon atoms or a group ($R_{16a}$)($R_{17a}$)($R_{18a}$)N—($CH_2$)$_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms; and $X^-$ is an anion chosen from the group of halides, acetates, phosphates, nitrates and methyl sulfates. Such compounds are, for example, FINQUAT CT-P, sold by the company FINTEX (Quaternium 89), and FINQUAT CT, sold by the company FINETEX (Quaternium 75).

Examples of cationic/cationizable surfactants, which may be incorporated in certain instances, include those having a structure in accordance with the general formula provided below:

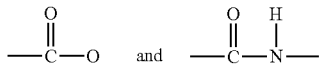

wherein R4 is a saturated or unsaturated, straight or branched alkyl chain with 8 to 24 C atoms, R5 is a straight or branched alkyl chain with 1 to 4 C atoms, A is selected from:

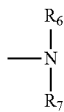

and B is selected from:

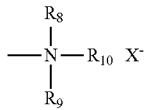

wherein $R_6$ and $R_7$ are the same or different and are H or an alkyl chain with 1 to 4 C atoms, hydroxyl alkyl chain with 1 to 4 C atoms and di hydroxyl alkyl chain with 2 to 4 C atoms, $R_8$ and $R_9$ are the same or different, an alkyl chain with 1 to 4 C atoms, hydroxyl alkyl chain with 1 to 4 C atoms and di hydroxyl alkyl chain with 2 to 4 C atoms, $R_{10}$ is an alkyl chain with 1 to 4 C atoms, hydroxyl alkyl chain with 1 to 4 C atoms or di hydroxyl alkyl chain with 2 to 4 C atoms.

In some instances, $R_4$ is saturated or unsaturated, straight or branched alkyl chain with 10 to 24 C atoms, more preferably 12 to 22 C atoms and $R_5$ is straight or branched alkyl group with 1 to 4 C atoms, and A, B, $R_6$ to $R_{10}$ are same as above.

Non-limiting suitable examples are stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl dimethylamine, stearamidopropyl diethylamine, stearamidopropyldibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palm itylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxylmonium methosulfate, and dicocoylethylhydroxyethylmonium methosulfate.

Cationizable surfactants may be chosen from fatty alkylamines, preferably, fatty dialkylamines. Non-limiting examples include dimethyl lauramine, dimethyl behenamine, dimethyl cocamine, dimethyl myristamine, dimethyl palmitamine, dimethyl stearamine, dimethyl tallowamine, dimethyl soyamine, and mixtures thereof.

Fatty dialkylamines include fatty amidoamine compounds, their salts, and mixtures thereof. Non-limiting examples include oleamidopropyl dimethylamine, linoleamidopropyl dimethylamine, isostearamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, and palmitamidopropyl dimethylamine.

Non-polymeric, mono-, di-, and/or tri-carboxylic acids may be used to "neutralize" the fatty dialkylamines. In some cases, the one or more non-polymeric, mono-, di-, and/or tri-carboxylic acids include at least one dicarboxylic acid. Non-limiting examples include lactic acid, oxalic acid, malonic acid, malic acid, glutaric acid, citric acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, benzoic acid, and mixtures thereof. In particular, lactic acid or tartaric acid or mixtures thereof are useful, especially in combination with fatty dimethylamines such as, for example, stearamidopropyl dimethylamine.

In an embodiment, hair composition may be formulated with a cationic surfactant chosen from behentrimonium chloride, cetrimonium chloride, behentrimonium methosulfate, or mixtures thereof.

The hair composition may be formulated such that the two or more cationic surfactants are associated with the same or different balancing anionic ions. For example, at least one of the two or more cationic surfactants may have a chloride ion and/or a sulfate ion. In some instances, the two or more cationic surfactants comprise cetrimonium chloride and one or both of behentrimonium methosulfate and behentrimonium chloride. In further instances, the two or more cationic surfactants comprise behentrimonium chloride and one or both of behentrimonium methosulfate and cetrimonium chloride.

Acid(s)

The hair compositions may include one or more non-fatty acids. The amount of non-fatty acids present in the hair composition may be, e.g., about 0.01 to about 8 wt. %, about 0.01 to about 6 wt. %, about 0.01 to about 5 wt. %, about 0.01 to about 4 wt. %, about 0.01 to about 3 wt. %, about 0.01 to about 2 wt. %, about 0.01 to about 1 wt. %; about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.25 to about 8 wt. %, about 0.25 to about 6 wt. %, about 0.25 to about 5 wt. %, about 0.25 to about 4 wt. %, about 0.25 to about 3 wt. %, about 0.25 to about 2 wt. %, about 0.25 to about 1 wt. %; about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 0.75 to about 8 wt. %, about 0.75 to about 6 wt. %, about 0.75 to about 5 wt. %, about 0.75 to about 4 wt. %, about 0.75 to about 3 wt. %, about 0.75 to about 2 wt. %; about 1 to about 8 wt. %, about 1 to about 6 wt. %, about 1 to about 5 wt. %, about 1 to about 4 wt. %, about 1 to about 3 wt. %, or about 1 to about 2 wt. %, including ranges and subranges therebetween, based on the total weight of the hair composition.

Preferably, the acids are chosen from citric acid, tartaric acid, lactic acid, and a mixture thereof. In some instances, the acids are chosen from tartaric acid, lactic acid, and a mixture thereof. The inventors unexpectedly discovered that certain embodiments of the hair compositions, which included one or more acids chosen from citric acid, tartaric acid, lactic acid, and a mixture thereof, exhibited enhanced color stability. The inventors were surprised by the enhanced color stability and solubility of certain hair compositions comprising an acid chosen from tartaric acid, lactic acid, and a mixture thereof.

pH Adjuster(s)

The hair composition may include one or more pH adjusters to increase or decrease the overall pH of the hair composition. For example, one or more acids may be included to decrease the pH of the hair composition. Examples of suitable acids for decreasing the pH of the hair composition include, but are not limited to, citric acid, acetic acid, and the like. The hair composition may include one or more bases, such as sodium hydroxide, potassium hydroxide and the like, to increase the pH of the hair composition. Additional or alternative acids and bases that are suitable for adjusting the pH of the hair composition are readily known to one of ordinary skill in the art.

The amount of the pH adjuster in the hair composition may be based on the desired pH of the final hair composition and/or product. For example, the hair composition may have an amount of pH adjusters such that the pH of the composition is about 3 to about 9, preferably about 4 to about 8, preferably about 4 to about 7, preferably about 4 to about 6, or preferably about 4 to about 5.

The amount of the pH adjuster in the hair composition may be based on the desired pH of the final hair composition and/or product. For example, the total amount of the pH adjuster may range from about 0.05 to about 20 wt. %, based on the total weight of the hair composition. In some instances, the total amount of pH adjuster is from about 0.05 to about 15 wt. %, about 0.1 to about 10 wt. %, or about 0.12 to about 5 wt. %, including ranges and sub-ranges therebetween, based on the total weight of the hair composition.

Chelant(s)

The hair composition may, optionally, include chelant(s). As used herein, chelant(s) may be referred to as chelating agent(s). The amount of chelants present in the hair composition may be, e.g., about 0.01 to about 20 wt. %, about 0.01 to about 15 wt. %, about 0.01 to about 10 wt. %, about 0.01 to about 8 wt. %, about 0.01 to about 6 wt. %, about 0.01 to about 5 wt. %, about 0.01 to about 4 wt. %, about 0.01 to about 3 wt. %, about 0.01 to about 2 wt. %, about 0.01 to about 1 wt. %; about 0.1 to about 20 wt. %, about 0.1 to about 15 wt. %, about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.25 to about 20 wt. %, about 0.25 to about 15 wt. %, about 0.25 to about 10 wt. %, about 0.25 to about 8 wt. %, about 0.25 to about 6 wt. %, about 0.25 to about 5 wt. %, about 0.25 to about 4 wt. %, about 0.25 to about 3 wt. %, about 0.25 to about 2 wt. %, about 0.25 to about 1 wt. %; about 0.5 to about 20 wt. %, about 0.5 to about 15 wt. %, about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 0.75 to about 20 wt. %, about 0.75 to about 15 wt. %, about 0.75 to about 10 wt. %, about 0.75 to about 8 wt. %, about 0.75 to about 6 wt. %, about 0.75 to about 5 wt. %, about 0.75 to about 4 wt. %, about 0.75 to about 3 wt. %, about 0.75 to about 2 wt. %; about 1 to about 20 wt. %, about 1 to about 15 wt. %, about 1 to about 10 wt. %, about 1 to about 8 wt. %, about 1 to about 6 wt. %, about 1 to about 5 wt. %, about 1 to about 4 wt. %, about 1 to about 3 wt. %, or about 1 to about 2 wt. %, including ranges and subranges therebetween, based on the total weight of the hair composition.

In some cases, the chelant may be chosen from glutamic acid, diacetic acid, and a mixture thereof. In at least one preferred embodiment, the chelant is tetrasodium glutamate diacetate.

Non-limiting examples of chemical chelating agents include aminotrimethyl phosphonic acid, β-alanine diacetic acid, cyclodextrin, cyclohexanediamine tetracetic acid, diethylenetriamine pentamethylene phosphonic acid, diethanolamine N-acetic acid, ethylene diamine tetracetic acid (EDTA or $YH_4$) and its sodium ($YH_3Na$, $Y_2H_2Na_2$, $YHNa_3$ and $YNa_4$), potassium ($YH_3K$, $Y_2H_3K_3$ and $YK_4$), calcium disodium, and diammonium salts and its salts with triethanolamine (TEA-EDTA), etidronic acid, galactanic acid, hydroxyethyl ethylenediamine tetracetic acid (HEDTA) and its trisodium salt, gluconic acid, glucuronic acid, nitrilotriacetic acid (NTA) and its trisodium salt, pentetic acid, phytic acid, ribonic acid, diammonium citrate, disodium azacycloheptane diphosphonate, disodium pyrophoshate, hydroxypropyl cyclodextrin, methyl cyclodextrin, pentapotassium triphosphate, pentasodium aminotrimethylene phosphonate, pentasodium ethylenediamine tetramethylene phosphonate, pentasodium pentetate, pentasodium triphosphate, potassium citrate, potassium EDTMP, sodium EDTMP, sodium chitosan methylene phosphonate, sodium hexametaphosphate, sodium metaphosphate, potassium polyphosphate, sodium polyphosphate, sodium trimetaphosphate, sodium dihydroxyethylglycinate, potassium gluconate, sodium gluconate, sodium glucopeptate, sodium glycereth-1 polyphosphate, tetrapotassium pyrophosphate, triethanolamine polyphosphate (TEA), tetrasodium pyrophosphate, trisodium phosphate, potassium triphosphonomethylamine oxide, sodium metasilicate, sodium phytate, sodium polydimethylglycinophenolsulfonate, tetrahydroxyethyl ethylene diamine, tetrahydroxypropyl ethylene diamine, tetrapotassium etidronate, tetrasodium etidronate, tetrasodium iminodisuccinate, trisodium ethylenediamine disuccinate, ethanolamine N,N-diacetic acid, disodium acetate, dimercaprol, deferoxamine, Zylox, and/or iron chelating agent disclosed and claimed in the international patent application WO 94/61338, which is incorporated herein in its entirety for all purposes. Examples of biological chelating agents include metallothionein, transferrin, calmodulin, and sodium chitosan methylene phosphonate. In at least one instance, the chelating agent is trisodium ethylenediamine disuccinate.

Preservative(s)

Preservatives may be included in the hair composition in an amount typically from about 0.01 to about 20 wt. %, about 0.01 to about 18 wt. %, about 0.01 to about 16 wt. %, about 0.01 to about 14 wt. %, about 0.01 to about 12 wt. %, about 0.01 to about 10 wt. %, about 0.01 to about 8 wt. %, about 0.01 to about 7 wt. %, about 0.01 to about 6 wt. %, about 0.01 to about 5 wt. %; about 0.1 to about 20 wt. %, about 0.1 to about 18 wt. %, about 0.1 to about 16 wt. %, about 0.1 to about 14 wt. %, about 0.1 to about 12 wt. %, about 0.1 to about 10 wt. %, about 0.1 to about 8 wt. %, about 0.1 to about 7 wt. %, about 0.1 to about 6 wt. %, about 0.1 to about 5 wt. %; about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 1 to about 7 wt. %, about 1 to about 6 wt. %, about 1 to about 5 wt. %; about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. %, or about 4 to about 7 wt. %, including all ranges and sub-ranges therebetween, based on the total weight of the hair composition. Non-limiting examples of preservatives include sodium benzoate, potassium sorbate, phenoxyethanol, salicylic acid, tocopherol, chlorphenesin, BHT, disodium EDTA, pentaerythrityl tetra-di-t-butyl hydroxyhydrocinnamate, and mixtures thereof.

Miscellaneous Ingredient(s)

The hair compositions may include one or more miscellaneous ingredients, such as colorants, opacifier, absorbents, active ingredients, fragrances, extracts (e.g. natural extracts), fillers (e.g., organic fillers, inorganic fillers, silica, mica, etc.), or the like. The total amount of miscellaneous ingredients is typically about 15 wt. % or less, based on the total weight of the hair compositions. For example, the hair composition may include miscellaneous ingredients in an amount of about 12.5 wt. % or less, about 10 wt. % or less, about 8 wt. % or less, about 6 wt. % or less, about 5 wt. % or less, about 4 wt. % or less, about 3 wt. % or less, about 2 wt. % or less, or about 1 wt. % or less, based on the total weight of the hair composition. In some instances, the amount of miscellaneous ingredients present in the hair composition is about 0.01 to about 15 wt. %, about 0.01 to about 12.5 wt. %, about 0.01 to about 10 wt. %, about 0.01 to about 8 wt. %, about 0.01 to about 6 wt. %, about 0.01 to about 5 wt. %, about 0.01 to about 4 wt. %, about 0.01 to about 3 wt. %, about 0.01 to about 2 wt. %, about 0.01 to about 1 wt. %; about 0.1 to about 15 wt. %, about 0.1 to about 12.5 wt. %, about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.5 to about 15 wt. %, about 0.5 to about 12.5 wt. %, about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 1 to about 15 wt. %, about 1 to about 12.5 wt. %, about 1 to about 10 wt. %, about 1 to about 8 wt. %, about 1 to about 6 wt. %, about 1 to about 5 wt. %, about 1 to about 4 wt. %, about 1 to about 3 wt. %, about 1 to about 2 wt. %; about 2 to about 15 wt. %, about 2 to about 12.5 wt. %, about 2 to about 10 wt. %, about 2 to about 8 wt. %, about 2 to about 6 wt. %, about 2 to about 5 wt. %, about 2 to about 4 wt. %; about 4 to about 15 wt. %, about 4 to about 12.5 wt. %, about 4 to about 10 wt. %, about 4 to about 8 wt. %, about 4 to about 6 wt. %; about 6 to about 15 wt. %, about 6 to about 12.5 wt. %, about 6 to about 10 wt. %, about 6 to about 8 wt. %; about 8 to about 15 wt. %, about 8 to about 12.5 wt. %, about 8 to about 10 wt. %; about 10 to about 15 wt. %, about 10 to about 12.5 wt. %; or about 12 to about 15 wt. %, including any ranges and subranges therebetween, based on the total weight of the hair composition.

The hair compositions of the instant disclosure may be incorporated into a kit. For example, the kits may include at least one hair composition according to the instant disclosure and one or more additional compositions, for example, a shampoo, a conditioner, etc. The various compositions are separately contained in the kits. In some instances, the kits include one or more hair compositions according the instant disclosure, a shampoo, a conditioner a mask, and/or other hair treatment product, all of which are separately contained. Instructions, mixing components, measuring tools, etc., may also optionally be included in the kits.

The compositions may be packaged in a variety of different containers, such as, for example, a ready-to-use container. Non-limiting examples of useful packaging include tubes, jars, caps, unit dose packages, and bottles, including squeezable tubes, bottles, and sprayable containers. The packaging may be configured so that it can be attached to a wall, such as a wall in a bathroom, including walls of a shower or tub. For example, the packaging can be a container that is configured to attach to a wall, such that when pressure is applied to the container, the composition contained therein is expelled from one or more openings in the container. In some cases, the packaging is a tube, such as a tube with two compartments, or dual tubes, each forming a separate compartment. Each compartment may include a different composition. For example, one tube or compartment may include a hair composition according to the instant disclosure, and the other tube may include a composition to be used with the hair composition, for example, a shampoo, a conditioner, an all-in-one shampoo/conditioner (i.e., a conditioning shampoo; also referred to as a "co-wash") mask or other hair treatment products.

Methods of Treating Hair

Aspects of the instant disclosure also relate to methods for making and using such hair compositions. A method for treating and conditioning hair according to aspects of the disclosure typically includes:

(I) applying a hair composition to wet or dam hair, the hair composition comprising:
  (a) about 50 to about 90 wt. % of a polyol;
  (b) about 0.1 to about 10 wt. % of fatty compounds, the fatty compounds comprising one or more fatty ethers and one or more carbonates,
    wherein a weight ratio of the total amount of carbonate to the total amount of fatty ether is about 3:1 to about 1:1,
  (c) about 10 to about 35 wt. % of a monoalcohol; and
  (d) about 0.1 to about 5 wt. % of a cationic surfactant,
    wherein all weight percentages are based on the total weight of the hair composition.

The methods for treating and/or conditioning hair according to the disclosure may vary, but typically include applying a hair composition as disclosed herein, allowing the hair composition to remain on the hair for a sufficient amount of time, and rinsing the hair compositions from the hair. The hair composition may be applied to the hair in a sequence with other compositions. For example, the hair composition may be applied to the hair (wet or dry) before shampooing the hair, after shampooing the hair, before applying a conditioner to the hair, and/or after applying a conditioning to the hair, etc. The hair compositions, however, are not required to be used in a sequence.

In some cases, the hair compositions are used in conjunction with additional hair compositions in a routine, for example, during an individual's normal showering/bathing routine. The hair composition may be applied to the hair individually or may be combined with one or more additional compositions. For instance, the hair composition may be mixed with a shampoo (or conditioner) prior to application to the hair. In this case, the mixture of the shampoo (or conditioner) and the hair composition are simultaneously applied to the hair during the cleansing or conditioning process and simultaneously rinsed from the hair. Alternatively, the hair composition may be layered on top of (or lathered into) hair to which a shampoo (or conditioner) has already been applied or vice versa. In this case, the shampoo (or conditioner) may be first applied to the hair and without rinsing the shampoo (or conditioner) from the hair, the hair composition is also applied to the hair. Alternatively, the hair composition may be applied to the hair and without rinsing it from the hair, a shampoo (or conditioner) is then subsequently applied to the hair.

When used in conjunction with a shampoo and/or a conditioner, the hair composition may be mixed or used with the shampoo and/or conditioner in a ratio of about 1:10 to about 10:1, about 1:5 to about 5:1, about 1:3 to about 3:1, about 1:2 to about 2:1, about 1:1 to about 4:1, about 1:1 to about 3:1, or about 1:1 to about 2:1 (hair composition of the instant disclosure: shampoo/conditioner, etc.).

The hair compositions of the instant disclosure may be allowed to remain on the hair for a minimum amount of time before being rinsed from the hair, but it is not necessary to allow the hair composition to remain on the hair for an extended period of time. Conveniently, the hair compositions can be applied and allowed to remain on the hair for a period of time that is typical for regular shampooing and/or conditioning. For example, the hair composition (whether combined with another hair-treatment composition such as a shampoo or conditioner) may be applied to the hair and allowed to remain on the hair for a few seconds (1, 2, 3, or 5 seconds) up to about 1 minute, about 2 minutes, about 5 minutes, about 10 minutes, about 15 minutes, about 20 minutes, about 25 minutes, or about 30 minutes.

When the hair composition is not being mixed with another composition prior to application to the hair, the hair composition may be applied to the hair immediately after or before the hair is treated with another composition (e.g., a shampoo and/or a conditioner). For example, the hair compositions may be applied to the hair within about a few seconds or 1, 2, 5, 10, or 20 minutes before or after a shampoo and/or a conditioner is applied to the hair.

The method, when treating hair, may include conditioning the hair; providing curl definition to the hair; providing frizz control to the hair; improving ease of combability and detangling; protecting the hair from damage; increasing the appearance of hair volume; imparting or improving shine on hair; or a combination thereof.

EMBODIMENTS OF THE DISCLOSURE

According to certain embodiments, provided is a hair composition comprising:
  about 50 to about 90 wt. %, preferably about 60 to about 90 wt. %, more preferably about 60 to about 87 wt. %, of a polyol, such as those chosen from ethylene glycol, propylene glycol, butylene glycol, hexylene glycol, pentylene glycol, diethylene glycol, dipropylene glycol, 1,3 propanediol, glycerin, diglycerin, and a mixture thereof;
  about 0.1 to about 10 wt. %, preferably about 0.5 to about 10 wt. %, more preferably about 0.5 to about 8 wt. %, of fatty compounds, the fatty compounds comprising a carbonate and a fatty ether,
  wherein a weight ratio of the total amount of carbonate to the total amount of fatty ether is about 3:1 to about 1:1, preferably about 2:1 to about 1:1,
  about 10 to about 35 wt. %, preferably about 10 to about 33 wt. %, more preferably about 10 to about 30 wt. %, of one or more monoalcohols having from 2 to 6 carbon atoms, preferably selected from ethanol, butanol, pentanol, hexanol, isopropyl alcohol, cyclohexanol, isobutyl alcohol, 2-methyl-2-butanol (2-methylbutan-2-ol), and a mixture thereof; and about 0.1 to about 5 wt. %, preferably about 0.1 to about 9 wt. %, more preferably about 0.5 to about 9 wt. % of a cationic surfactant, preferably, chosen from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, stearamidopropyl dimethylamine, isostearamidopropyl dimethylamine, oleyl hydroxyethyl imidazoline, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and a mixture thereof, wherein all weight percentages are based on the total weight of the hair composition.

In accordance with another embodiment, provided is a hair composition comprising:

about 50 to about 90 wt. %, preferably about 60 to about 90 wt. %, more preferably about 60 to about 87 wt. %, of a polyol, such as those chosen from ethylene glycol, propylene glycol, butylene glycol, hexylene glycol, pentylene glycol, diethylene glycol, dipropylene glycol, 1,3 propanediol, glycerin, diglycerin, and a mixture thereof;

about 0.1 to about 10 wt. %, preferably about 0.5 to about 10 wt. %, more preferably about 0.5 to about 8 wt. %, of fatty compounds, the fatty compounds comprising a carbonate and a fatty ether, about 10 to about 35 wt. %, preferably about 10 to about 33 wt. %, more preferably about 10 to about 30 wt. %, of one or more monoalcohols having from 2 to 6 carbon atoms, preferably selected from ethanol, butanol, pentanol, hexanol, isopropyl alcohol, cyclohexanol, isobutyl alcohol, 2-methyl-2-butanol (2-methylbutan-2-ol), and a mixture thereof;

about 0.1 to about 5 wt. %, preferably about 0.1 to about 9 wt. %, more preferably about 0.5 to about 9 wt. % of a cationic surfactant, preferably, chosen from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, stearamidopropyl dimethylamine, isostearamidopropyl dimethylamine, oleyl hydroxyethyl imidazoline, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and a mixture thereof; and about 0.01 to about 8 wt. %, preferably about 0.1 to about 8 wt. %, more preferably about 0.1 to about 6 wt. %, of an acid chosen from citric acid, tartaric acid, lactic acid, a salt thereof, and a mixture thereof, wherein all weight percentages are based on the total weight of the hair composition.

According to further embodiments, a method is provided for treating hair comprising:

(I) applying a hair composition to wet or damp hair, the hair composition comprising:

about 50 to about 90 wt. %, preferably about 60 to about 90 wt. %, more preferably about 60 to about 87 wt. %, of a polyol, such as those chosen from ethylene glycol, propylene glycol, butylene glycol, hexylene glycol, pentylene glycol, diethylene glycol, dipropylene glycol, 1,3 propanediol, glycerin, diglycerin, and a mixture thereof;

about 0.1 to about 10 wt. %, preferably about 0.5 to about 10 wt. %, more preferably about 0.5 to about 8 wt. %, of fatty compounds, the fatty compounds comprising a carbonate and a fatty ether, wherein a weight ratio of the total amount of carbonate to the total amount of fatty ether is about 3:1 to about 1:1, preferably about 2:1 to about 1:1, about 10 to about 35 wt. %, preferably about 10 to about 33 wt. %, more preferably about 10 to about 30 wt. %, of one or more monoalcohols having from 2 to 6 carbon atoms, preferably selected from ethanol, butanol, pentanol, hexanol, isopropyl alcohol, cyclohexanol, isobutyl alcohol, 2-methyl-2-butanol (2-methylbutan-2-ol), and a mixture thereof; and about 0.1 to about 5 wt. %, preferably about 0.1 to about 9 wt. %, more preferably about 0.5 to about 9 wt. % of a cationic surfactant, preferably, chosen from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, stearamidopropyl dimethylamine, isostearamidopropyl dimethylamine, oleyl hydroxyethyl imidazoline, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and a mixture thereof, wherein all weight percentages are based on the total weight of the hair composition.

The terms "comprising," "having," and "including" are used in their open, non-limiting sense. The terms "a" and "the" are understood to encompass the plural as well as the singular. The compositions and methods of the present disclosure can comprise, consist of, or consist essentially of the essential elements and limitations of the disclosure described herein, as well as any additional or optional ingredients, components, or limitations described herein or otherwise useful.

All percentages, parts and ratios herein are based upon the total weight of the compositions of the present disclosure, unless otherwise indicated. All ranges and values disclosed herein are inclusive and combinable. The expression "inclusive" for a range of concentrations means that the limits of the range are included in the defined interval. For examples, any value or point described herein that falls within a range described herein can serve as a minimum or maximum value to derive a sub-range, etc. Furthermore, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Other than in the operating examples, or where otherwise indicated, all numbers expressing quantities of ingredients and/or reaction conditions are to be understood as being modified in all instances by the term "about," meaning within +/−5% of the indicated number.

As used herein, the expression "at least one" is interchangeable with the expression "one or more" and thus includes individual components as well as mixtures/combinations.

The term "substantially free" or "essentially free" as used herein means that there is less than about 5% by weight of a specific material added to a composition, based on the total weight of the compositions. Nonetheless, the compositions may include less than about 2 wt. %, less than about 1 wt. %, less than about 0.5 wt. %, less than about 0.1 wt. %, less than 0.01 wt. %, or none of the specified material.

The term "active material" as used herein with respect to the percent amount of an ingredient or raw material, refers to 100% activity of the ingredient or raw material.

Throughout the disclosure, the term "a mixture thereof" may be used following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included. The salts referred to throughout the disclosure may include salts having a counter-ion such as an alkali metal, alkaline earth metal, or ammonium counter-ion. This list of counter-ions, however, is non-limiting.

"Volatile", as used herein, means having a flash point of less than about 100° C. "Non-volatile", as used herein, means having a flash point of greater than about 100° C.

The term "polymers," as defined herein, include homopolymers and copolymers formed from at least two different types of monomers.

The term "INCI" is an abbreviation of International Nomenclature of Cosmetic Ingredients, which is a system of names provided by the International Nomenclature Committee of the Personal Care Products Council to describe personal care ingredients.

All components and elements positively set forth in this disclosure can be negatively excluded from the claims. In other words, the compositions (nanoemulsions) of the instant disclosure can be free or essentially free of all components and elements positively recited throughout the instant disclosure.

Some of the various categories of components identified may overlap. In such cases where overlap may exist and the composition includes both components (or the composition includes more than two components that overlap), an overlapping compound does not represent more than one component. For example, a fatty acid may be characterized as both a nonionic surfactant and a fatty compound. If a particular composition includes both a nonionic surfactant and a fatty compound, a single fatty acid will serve as only the nonionic surfactant or as only the fatty compound (the single fatty acid does not serve as both the nonionic surfactant and the fatty compound).

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

EXAMPLES

Implementation of the present disclosure is provided by way of the following examples. The following examples serve to elucidate aspects of the technology without being limiting in nature.

Example 1

Exemplary Compositions

Ten non-limiting, exemplary compositions (Ex. A-H) were prepared in accordance with aspects of the disclosure. The formulations for Example Compositions A-H are shown in Table 1.

TABLE 1

|   |   | INCI US Name | Ex. A | Ex. B | Ex. C | Ex. D |
|---|---|---|---|---|---|---|
| (a) | Polyol | PROPYLENE GLYCOL | 74.3 | 70.4 | 74.4 | 75.4 |
| (b) | Fatty Compounds | PROPYLENE GLYCOL DICAPRYLATE/DICAPRATE | 0.5 | 0.5 | 0.5 | 0.5 |
|   |   | DICAPRYLYL ETHER | 0.5 | 0.5 | 0.5 | 0.5 |
|   |   | CETYL ALCOHOL | 1.5 | 1.5 | 1.5 | 1.5 |
|   |   | DICAPRYLYL CARBONATE | 0.9 | 0.9 | 0.9 | 0.9 |
| (c) | Mono-alcohol | Ethanol | 20 | 25 | 20 | 20 |
| (d) | Cationic Surfactant | STEARAMIDOPROPYL DIMETHYLAMINE | 1.2 | 1.2 | 1.2 | 1.2 |
|   | Preservative | TOCOPHEROL | <0.1 | <0.1 | <0.1 | <0.1 |
|   | Fragrance | FRAGRANCE | 1.2 |   | 1 |   |

TABLE 1-continued

|   | | INCI US Name | Ex. E | Ex. F | Ex. G | Ex. H |
|---|---|---|---|---|---|---|
| (a) | Polyol(s) | PROPYLENE GLYCOL | 74.4 | 69.4 | 74.1 | 74.4 |
|   |   | PENTYLENE GLYCOL |   |   |   | <0.1 |
| (b) | Fatty Compounds | PROPYLENE GLYCOL DICAPRYLATE/DICAPRATE | 0.5 | 0.5 | 0.5 | 0.5 |
|   |   | DICAPRYLYL ETHER | 0.5 | 0.5 | 0.5 | 0.5 |
|   |   | CETYL ALCOHOL | 1.5 | 1.5 | 1.5 | 1.5 |
|   |   | DICAPRYLYL CARBONATE | 0.9 | 0.9 | 0.9 | 0.9 |
| (c) | Mono-alcohol | Ethanol | 20 | 25 | 20 | 20 |
| (d) | Cationic Surfactant | STEARAMIDOPROPYL DIMETHYLAMINE | 1.2 | 1.2 | 1.2 | 1.2 |
| (f) | Chelant | TETRASODIUM GLUTAMATE DIACETATE |   |   | 0.1 |   |
|   | Preservative | TOCOPHEROL | <0.1 | <0.1 | <0.1 | <0.1 |
|   | Fragrance | FRAGRANCE | 1 | 1 | 1.2 | 1 |
|   | Misc. | ARGANIA SPINOSA KERNEL OIL |   |   |   | <0.1 |
|   |   | HYDROLYZED SOY PROTEIN |   |   |   | <0.1 |
|   | Water | WATER |   |   | 0.1 | <0.1 |

Example Compositions A-H were evaluated to assess their color stability and solubility stability. In particular, samples of Example Compositions A-H underwent the following testing conditions: samples were kept for up to 8 weeks at a temperature of 4° C., 25° C., or 45° C.

Example Compositions A-D each exhibited stable solvation with no crystal formation or separation under the foregoing testing conditions. Example Compositions A-C exhibited minor color change. Example Composition D did not exhibit color change. Example Compositions E-H did not exhibit crystals, but had a minor amount of oil that separated from the emulsion.

Example 2

Comparative Compositions

Seven comparative compositions (Comp. 1, 6, and 10) and three compositions (FLAS. 7-9) were prepared according to the formulations presented in Table 2.

TABLE 2

|   | | INCI US Name | Comp. 1 | Comp. 2 | Comp. 3 | Comp. 4 | Comp. 5 |
|---|---|---|---|---|---|---|---|
| (a) | Polyol | PROPYLENE GLYCOL | 75.4 | 74.4 | 74.25 | 74.3 | 74.4 |
| (b) | Fatty Compounds | PROPYLENE GLYCOL DICAPRYLATE/DICAPRATE | 0.5 | 0.5 | 0.5 | 0.5 |   |
|   |   | DICAPRYLYL ETHER | 0.5 | 0.5 | 0.5 | 0.5 | 0.5 |
|   |   | CETYL ALCOHOL | 1.5 | 1.5 | 1.5 | 1.5 | 1.5 |
|   |   | DICAPRYLYL CARBONATE |   |   |   |   | 0.9 |
|   |   | ISOPROPYL MYRISTATE |   |   |   |   |   |
|   |   | HEXYL LAURATE | 0.9 | 0.9 | 0.9 | 0.9 |   |
|   |   | HEXYLDECANOL |   |   |   |   | 0.25 |
|   |   | HEXYLDECYL LAURATE |   |   |   |   | 0.25 |
| (c) | Mono-alcohol | ETHANOL | 20 | 20 | 20 | 20 | 20 |
| (d) | Cationic Surfactant | STEARAMIDOPROPYL DIMETHYLAMINE | 1.2 | 1.2 | 1.2 | 1.2 | 1.2 |
|   | Preservative | TOCOPHEROL | 0.00015 | 0.00015 | 0.00015 | 0.0006 | 0.0006 |
|   | Fragrance | FRAGRANCE |   | 1 | 1.15 | 1.2 | 1 |

|   | | INCI US Name | Comp. 6 | FLA. 7 | FLA. 8 | FLA. 9 | Comp. 10 |
|---|---|---|---|---|---|---|---|
| (a) | Polyol(s) | PROPYLENE GLYCOL | 74.4 | 74.6 | 74.3 | 74.3 | 72.7 |
|   |   | PENTYLENE GLYCOL |   |   |   |   |   |
| (b) | Fatty Compounds | PROPYLENE GLYCOL DICAPRYLATE/DICAPRATE |   | 0.2 | 0.4 | 0.3 |   |
|   |   | DICAPRYLYL ETHER |   | 0.5 | 0.6 | 0.7 |   |
|   |   | CETYL ALCOHOL | 1.5 | 1.5 | 1.5 | 1.5 |   |
|   |   | DICAPRYLYL CARBONATE |   | 0.9 | 0.9 | 0.9 | 0.9 |
|   |   | MYRISTYL ALCOHOL |   |   |   |   | 2 |
|   |   | ISOPROPYL ALCOHOL |   |   |   |   | 0.1 |
|   |   | HEXYL LAURATE |   |   |   |   |   |
|   |   | HEXYLDECANOL | 1 |   |   |   |   |
|   |   | HEXYLDECYL LAURATE | 1 |   |   |   |   |

TABLE 2-continued

| | | | | | | |
|---|---|---|---|---|---|---|
| (c) Mono-alcohol | Ethanol | 20 | 20 | 20 | 25 | 20 |
| (d) Cationic Surfactant | STEARAMIDOPROPYL DIMETHYLAMINE | 1.2 | 1.2 | 1.2 | 1.2 | |
| | CETRIMONIUM CHLORIDE | | | | | 0.6 |
| | BEHENTRIMONIUM CHLORIDE | | | | | 0.6 |
| (f) Chelant | TETRASODIUM GLUTAMATE DIACETATE | | | | | |
| Preservative | TOCOPHEROL | | <0.1 | <0.1 | <0.1 | <0.1 |
| | PHENOXYETHAOL | | | | | <0.1 |
| Fragrance | FRAGRANCE | 1 | 1.2 | 1.2 | 1.2 | 1.2 |
| Misc. | ARGININE PCA | | | | | <0.1 |
| | HYDROXYPROPYLTRIMONIUM HYDROLYZED WHEAT PROTEIN | | | | | <0.1 |
| Water | WATER | | | | | 1.9 |

Comparative Compositions 1-9 were evaluated to assess their color stability and solubility stability. In particular, samples of Comparative Compositions 1-9 underwent the following testing conditions: samples were kept for up to 8 weeks at temperatures of 4° C., 25° C., and 45° C.

Comparative Composition 5 had an unstable solvation. In particular, the oil of Comparative Composition 5 separated from the emulsion within 4 weeks of starting the testing conditions. Comparative Compositions 7-9 exhibited severe crystals that would solubilize when shaken.

Example 3

Exemplary Compositions

Four non-limiting, exemplary compositions (Ex. I-L) were prepared in accordance with aspects of the disclosure. Specifically, Example Compositions I-K were prepared by first producing samples of Example Composition C and then adding an acid to the sample of Example Composition C. Example L was prepared by first producing Example Composition C and then adding oleyl alcohol.

The formulations for Example Compositions L-M are provided in Table 3.

sitions I, K, and L each exhibited no color change under either of the testing conditions. Example Composition M exhibited a minimal color change. Example Compositions I and L exhibited severe crystals that required vigorous mixing to solubilize the crystals. Unexpectedly, Example Compositions J and K did exhibit minimal crystals that would solubilize upon minimal mixing. Example Composition N showed no crystals.

Example 4

Comparative Evaluation

Example Compositions C and M were evaluated in comparison to Comparative Composition 10. Specifically, volunteers received a varying amount from 8-12 grams depending on their hair length and density of either Example Compositions C or M on a first half of head of hair and received an equivalent amount of Comparative Composition 10 on the other half of head of hair. The samples were uniformly applied to the respective half of head of hair for each volunteer. The volunteers' hair was evaluated by expert evaluators.

The evaluators determined that during application the hair that received Comparative Composition 10 exhibited more

TABLE 3

| | | INCI US Name | Ex. I | Ex. J | Ex. K | Ex. L | Ex. M |
|---|---|---|---|---|---|---|---|
| (a) | Polyol | PROPYLENE GLYCOL | 74.1 | 74 | 73.9 | 73.4 | 74.4 |
| (b) | Fatty Compounds | PROPYLENE GLYCOL DICAPRYLATE/DICAPRATE | 0.5 | 0.5 | 0.5 | 0.5 | 0.5 |
| | | DICAPRYLYL ETHER | 0.5 | 0.5 | 0.5 | 0.5 | 0.5 |
| | | CETYL ALCOHOL | 1.5 | 1.5 | 1.5 | 1.5 | 1.5 |
| | | DICAPRYLYL CARBONATE | 0.9 | 0.9 | 0.9 | 0.9 | |
| | | OLEYL ALCOHOL | | | | 1 | |
| | | HEXYL LAURATE | | | | | 0.9 |
| (c) | Mono-alcohol | Ethanol | 20 | 20 | 20 | 20 | 20 |
| (d) | Cationic Surfactant | STEARAMIDOPROPYL DIMETHYLAMINE | 1.2 | 1.2 | 1.2 | 1.2 | 1.2 |
| (e) | Acid | CITRIC ACID | 0.3 | | | | |
| | | TARTARIC ACID | | 0.4 | | | |
| | | LACTIC ACID | | | 0.5 | | |
| | Preservative | TOCOPHEROL | <0.1 | <0.1 | <0.1 | <0.1 | <0.1 |
| | Fragrance | FRAGRANCE | 1 | 1 | 1 | 1 | 1 |
| | Water | WATER | | | | | |

Example Compositions I-L were evaluated to assess their color stability and solubility stability. In particular, samples of Example Compositions I-L underwent the following testing conditions: samples were kept for up to 8 weeks at a temperature of 4° C., 25° C., and 45° C. Example Composmoothness than the hair that received Example Composition C. Example Composition C provided a faster transformation than Comparative Composition 10. The hair that received Example Composition M exhibited a better topical feel than Comparative Composition 10.

During rinsing, Comparative Composition 10 provided more smoothness and detangling effect to the hair than Example Composition C. While the hair was wet, Example Composition C provided a better coating feel, and detangling effect to hair than Example Composition C. Additionally, the hair that received Example Composition C was sleeker than the hair that received Comparative Composition 10. The hair that received Example Composition M was more individualized and dried quicker than the hair that received Comparative Composition 10.

The hair was then dried and reevaluated. After drying, the hair that received Example Composition C had better volume, and was less frizzy than the hair that received Comparative Composition 10. The hair that received Example Composition M was weighed down less, had a lighter feel, exhibited more volume, and exhibited a better shine than the hair that received Comparative Composition 10. Additionally, the hair that received Example Composition M had better ends than the hair that received Comparative Composition 10.

Overall, it was determined that Example Composition C provided better care and repair, such as superior conditioning for damaged hair, than Comparative Composition 10. Example Composition M provided better discipline, manageability, and shine as compared to Comparative Composition 10. The hair that received Example Composition M was more lightweight than the Comparative Composition 10. A summary of the evaluation of Example Compositions C and M as well as Comparative Composition 10 is illustrated in FIG. 1.

The invention claimed is:

1. A hair composition comprising:
   (a) about 50 to about 90 wt. % of a glycol chosen from ethylene glycol, propylene glycol, butylene glycol, hexylene glycol, pentylene glycol, diethylene glycol, dipropylene glycol, or a mixture thereof;
   (b) about 0.1 to about 10 wt. % of fatty compounds, the fatty compounds comprising:
      (b)(i) a carbonate; and
      (b)(ii) a fatty ether;
         wherein (b)(i) and (b)(ii) are in a weight ratio of about 3:1 to about 1:1 ((b)(0):(b)(ii));
   (c) about 10 to about 35 wt. % of a monoalcohol having from 2 to 6 carbon atoms; and
   (d) about 0.1 to about 5 wt. % of a cationic surfactant;
      wherein the composition comprises less than 1 wt. % of water; and
      all weight percentages are based on a total weight of the composition.

2. The hair composition of claim 1 wherein (a) and (c) are in a weight ratio of about 9:1 to about 1.5:1 ((a):(c)).

3. The hair composition of claim 1 further comprising:
   (e) about 0.1 to about 5 wt. % of an acid chosen from citric acid, tartaric acid, lactic acid, a salt thereof, or a mixture thereof.

4. The hair composition of claim 3, wherein the acid is chosen from tartaric acid, lactic acid, a salt thereof, or a mixture thereof.

5. The hair composition of claim 1, wherein the glycol is propylene glycol.

6. The hair composition of claim 1, wherein the carbonate is dicaprylyl carbonate and the fatty ether is dicaprylyl ether.

7. The hair composition of claim 1, wherein the fatty compounds further comprise:
   (b)(iii) a fatty alcohol present in an amount up to 2 wt. %, wherein the fatty alcohol is chosen from cetearyl alcohol, stearyl alcohol, behenyl alcohol, cetyl alcohol, myristyl alcohol, isostearyl alcohol, lauryl alcohol, oleyl alcohol, or a mixture thereof.

8. The hair composition of claim 7, wherein (b)(iii) and (d) are in a weight ratio of about 2:1 to about 1:2.

9. The hair composition of claim 1, wherein the monoalcohol is ethanol.

10. The hair composition of claim 1, wherein the cationic surfactant is chosen from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, stearamidopropyl dimethylamine, isostearamidopropyl dimethylamine, oleyl hydroxyethyl imidazoline, behenamidopropyl dimethylamine, behenamidopropyl diethylamine, behenamidoethyl diethylamine behenamidoethyl dimethylamine, arachidamidopropyl diethylamine arachidamidoethyl diethylamine arachidamidoethyl dimethylamine, or a mixture thereof.

11. The hair composition of claim 3 further comprising:
   (f) about 0.1 to about 5 wt. % of a chelant.

12. The hair composition of claim 11, wherein the chelant is tetrasodium glutamate diacetate.

13. The hair composition of claim 3 further comprising:
   (f) about 0.1 to about 5 wt. % of tetrasodium glutamate diacetate.

14. A method for treating hair comprising applying a composition of claim 1 to wet or damp hair.

15. The method of claim 14, wherein treating the hair comprises:
   conditioning the hair;
   providing curl definition to the hair;
   providing frizz control to the hair;
   improving ease of combability and detangling;
   protecting the hair from damage;
   increasing appearance of hair volume;
   imparting or improving shine on the hair; or
   a combination thereof.

16. A hair composition comprising:
   (a) about 65 to about 85 wt. % of a of a glycol chosen from propylene glycol, butylene glycol, hexylene glycol, pentylene glycol, diethylene glycol, dipropylene glycol, or a mixture thereof;
   (b) about 1 to about 6 wt. % of fatty compounds, the fatty compounds comprising:
      (b)(i) a dialkyl carbonate;
      (b)(ii) a dialkyl ether;
         wherein (b)(i) and (b)(ii) are in a weight ratio of about 3:1 to about 1:1 ((b)(i)):(b(ii)); and
      (b)(iii) a fatty alcohol;
   (c) about 10 to about 35 wt. % of ethanol;
      wherein (a) and (c) are in a weight ratio of about 5:1 to about 2.5:1 ((a):(c));
   (d) about 0.5 to about 4 wt. % of a fatty dialkylamine;
      wherein (b)(i) and (d) are in a weight ratio of about 2:1 to about 1:2 ((b)(i):(d));
      the composition comprises less than 1 wt. % of water; and
      all weight percentages are based on a total weight of the composition.

17. The composition of claim 16, wherein the fatty dialkylamine is selected from oleamidopropyl dimethylamine, linoleamidopropyl dimethylamine, stearamidopropyl dimethylamine, isostearamidopropyl dimethylamine, behenamidopropyl dimethylamine, behenamidopropyl diethylamine, behenamidoethyl diethylamine, behenamidoethyl dimethylamine, arachidamidopropyl dimethylamine, arachidamidopropyl diethylamine, arachidamidoethyl diethylamine, arachidamidoethyl dimethylamine, or a mixture thereof.

18. The composition of claim 16, wherein the fatty dialkylamine is stearamidopropyl dimethylamine.

19. The composition of claim 18, wherein the fatty compounds comprise:
- (b)(i) dicaprylyl carbonate;
- (b)(ii) dicaprylyl ether;
  wherein (b)(i) and (b)(ii) are in a weight ratio of about 3:1 to about 1:1 ((b)(i)):(b(ii)); and
- (b)(ii) a fatty alcohol chosen from cetearyl alcohol, stearyl alcohol, behenyl alcohol, cetyl alcohol, myristyl alcohol, isostearyl alcohol, lauryl alcohol, oleyl alcohol, or a mixture thereof.

* * * * *

UNITED STATES PATENT AND TRADEMARK OFFICE
CERTIFICATE OF CORRECTION

PATENT NO. : 11,957,776 B2
APPLICATION NO. : 17/730382
DATED : April 16, 2024
INVENTOR(S) : Heather Lee, Jung Hyun Park and Kristin Jones It is certified that error appears in the above-identified patent and that said Letters Patent is hereby corrected as shown below:

In the Claims

Claim 1:
Should be changed as follows:
1. A hair composition comprising:
    (a) about 50 to about 90 wt.% of a glycol chosen from ethylene glycol, propylene glycol, butylene glycol, hexylene glycol, pentylene glycol, diethylene glycol, dipropylene glycol, or a mixture thereof;
    (b) about 0.1 to about 10 wt.% of fatty compounds, the fatty compounds comprising:
        (b)(i) a carbonate; and
        (b)(ii) a fatty ether;
            wherein (b)(i) and (b)(ii) are in a weight ratio of about 3:1 to about 1:1 ((b)(i): (b(ii);
    (c) about 10 to about 35 wt.% of a monoalcohol having from 2 to 6 carbon atoms; and
    (d) about 0.1 to about 5 wt.% of a cationic surfactant;
        wherein the composition comprises less than 1 wt.% of water; and
        all weight percentages are based on a total weight of the composition.

Signed and Sealed this
Twenty-second Day of October, 2024

Katherine Kelly Vidal
*Director of the United States Patent and Trademark Office*